United States Patent
Inoue et al.

(10) Patent No.: US 6,338,783 B1
(45) Date of Patent: Jan. 15, 2002

(54) GAS SENSOR, METHOD OF MANUFACTURING THE SAME, AND GAS SENSOR SYSTEM USING THE GAS SENSOR

(75) Inventors: Ryuji Inoue; Shoji Kitanoya; Tomohiro Fuma; Kenji Kato; Takafumi Oshima, all of Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 09/448,441

(22) Filed: Nov. 24, 1999

(30) Foreign Application Priority Data

Nov. 25, 1998 (JP) ............................................. 10-334108

(51) Int. Cl.[7] ............................................. G01N 27/407
(52) U.S. Cl. .................... 204/425; 204/426; 205/783.5; 205/787; 156/89.16
(58) Field of Search ................................. 204/424, 425, 204/426; 205/783.5, 784, 784.5, 785, 787; 73/23.31, 23.32; 156/89.11, 89.16, 89.12

(56) References Cited

U.S. PATENT DOCUMENTS

| 5,250,169 | A |   | 10/1993 | Logothetis et al. |   |
| 5,281,313 | A |   | 1/1994 | Visser et al. |   |
| 5,879,525 | A |   | 3/1999 | Kato | ............................. 204/424 |
| 5,893,968 | A |   | 4/1999 | Kato | ......................... 205/784.5 |
| 5,985,118 | A | * | 11/1999 | Makino et al. | .............. 204/426 |
| 6,036,841 | A | * | 3/2000 | Kato et al. | ................... 205/781 |
| 6,110,348 | A | * | 8/2000 | Sugiyama et al. | ........... 205/425 |
| 6,136,170 | A | * | 8/2000 | Inoue et al. | ................. 204/424 |
| 6,153,072 | A | * | 11/2000 | Inoue et al. | ................. 204/425 |

FOREIGN PATENT DOCUMENTS

| EP | 0841562 A2 | * | 5/1998 |
| EP | 0 902 279 A1 |   | 3/1999 |
| EP | 0 903 576 A2 |   | 3/1999 |

* cited by examiner

Primary Examiner—Robert J. Warden, Sr.
Assistant Examiner—Kaj K. Olsen
(74) Attorney, Agent, or Firm—Sughrue Mion, PLLC

(57) ABSTRACT

A gas sensor which can detect the concentration of a combustible gas component in a measurement gas with high accuracy even when the oxygen concentration of the measurement gas or the element temperature changes and which has an excellent response in detecting the combustible gas component is disclosed. In a gas sensor 1, the oxygen concentration of a measurement gas is adjusted to a predetermined level within a first processing space 9 through operation of a first oxygen pump element 3. The measurement gas having an adjusted oxygen concentration is then introduced into a second processing space 10, where a combustible gas component is burned through the assistance of electrodes 16 and 17 functioning as oxidation catalyst sections. Constant voltage is applied to a combustible gas component concentration detection element 5. In this state, when the amount of oxygen changes due to the combustion of the combustible gas component, the output current of the combustible gas component concentration detection element 5 changes with change in the amount of oxygen. Therefore, information regarding the combustible gas component concentration of the original measurement gas can be obtained from the value of the output current. Further, oxygen required to burn the combustible gas component within the second processing space 10 is supplemented by a second oxygen pump element 6. Unlike conventional apparatuses, no feedback system is used, and a variation in the concentration of the combustible gas component appears directly as a variation in the current of the combustible gas component concentration detection element 5. Therefore, a high detection response is obtained.

21 Claims, 22 Drawing Sheets

Fig. 7.

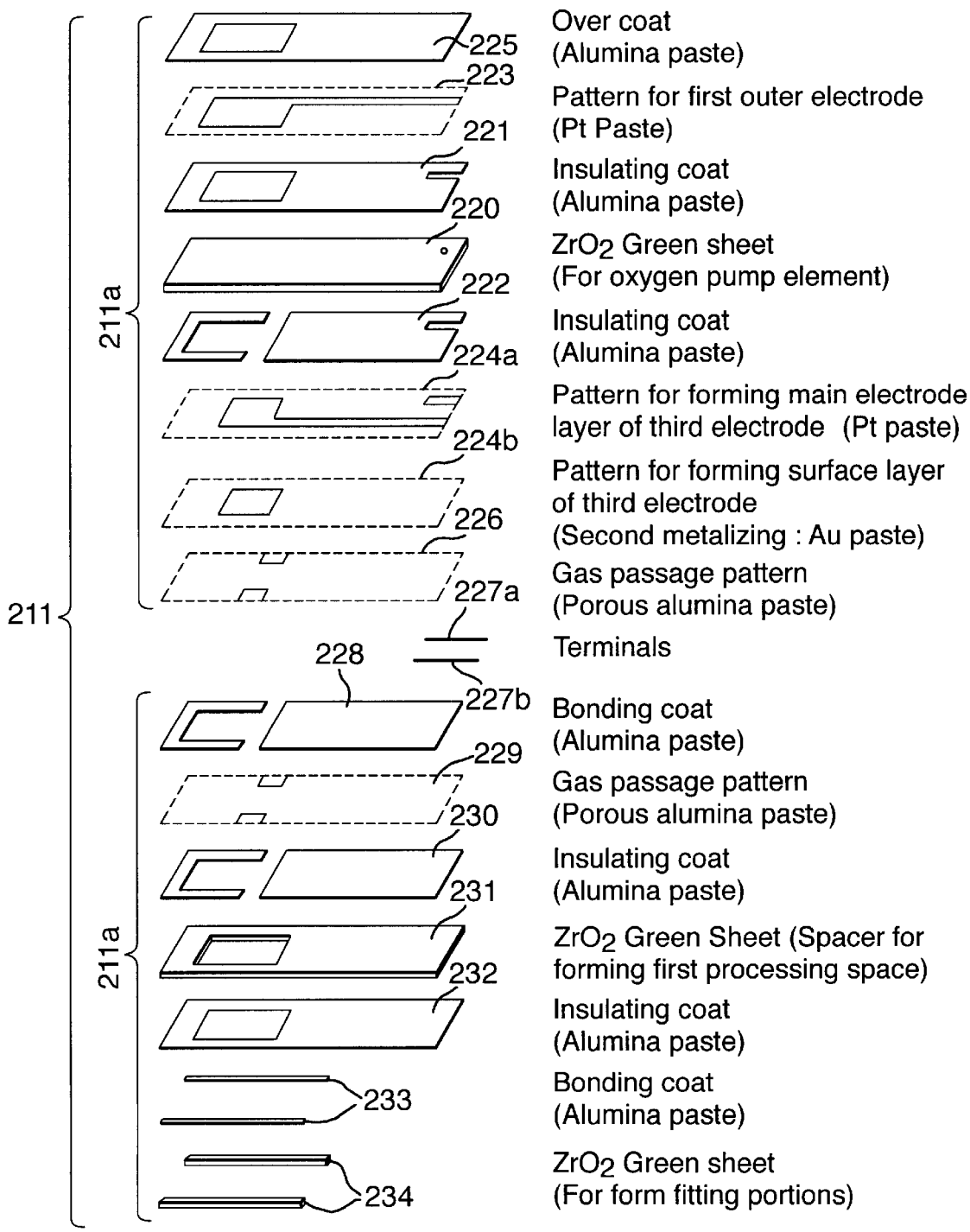

- 225 Over coat (Alumina paste)
- 223 Pattern for first outer electrode (Pt Paste)
- 221 Insulating coat (Alumina paste)
- 220 ZrO$_2$ Green sheet (For oxygen pump element)
- 222 Insulating coat (Alumina paste)
- 224a Pattern for forming main electrode layer of third electrode (Pt paste)
- 224b Pattern for forming surface layer of third electrode (Second metalizing : Au paste)
- 226 Gas passage pattern (Porous alumina paste)
- 227a Terminals
- 228 Bonding coat (Alumina paste)
- 227b Gas passage pattern (Porous alumina paste)
- 229 Insulating coat (Alumina paste)
- 230 ZrO$_2$ Green Sheet (Spacer for forming first processing space)
- 231 Insulating coat (Alumina paste)
- 232 Bonding coat (Alumina paste)
- 233 ZrO$_2$ Green sheet (For form fitting portions)
- 234

| Detected Current Id | $Id_1$ $Id_2$ $Id_3$ · · · · |
|---|---|
| HC Concentration | $C_1$ $C_2$ $C_3$ · · · · |

GAS SENSOR, METHOD OF MANUFACTURING THE SAME, AND GAS SENSOR SYSTEM USING THE GAS SENSOR

BACKGROUND OF THE INVENTION

The present invention relates to a gas sensor and a gas sensor system using the same.

Resistance-type sensors are known for measuring the concentration of a combustible gas component such as hydrocarbon (hereinafter may be referred to as HC) or CO contained in exhaust gas from an automobile or the like. For example, an oxide semiconductor (n type) such as $SnO_2$ or the like is used as a sensing element for measuring the concentration of a combustible gas component such as HC or CO. Specifically, oxygen in the atmosphere adsorbs on the sensing element through an effect induced by negative charges. When the atmosphere contains a combustible gas component such as HC or CO, the combustible gas component undergoes a combustion reaction with the adsorbing oxygen, thereby causing oxygen to be desorbed from the sensing element. Since a change in an electric resistance of the sensing element associated with the oxygen desorption depends on the combustible gas component concentration of the atmosphere, the combustible gas component concentration of the atmosphere can be obtained through measurement of the change of the electric resistance. However, such a resistance-type sensor has a drawback that an output from the sensing element formed of an oxide semiconductor is likely to vary depending on the concentration of oxygen or water vapor contained in an exhaust gas. Accordingly, even when the combustible gas component concentration remains unchanged, a detection output value varies depending on, for example, the oxygen concentration of the exhaust gas.

In order to solve the above problem, an apparatus for measuring a combustible gas component concentration having the following structure is disclosed in Japanese Patent Application Laid-Open No. 8-247995. In the apparatus, a sensing element has two processing zones. An exhaust gas is introduced into a first processing zone via first diffusion-controlling means. Oxygen is pumped out from the first processing zone by a first oxygen concentration adjustment pump element so as to reduce the oxygen concentration of the first processing zone to a low value at which a combustible gas component is not substantially burned. Next, the gas having the thus-reduced oxygen concentration is introduced into a second processing zone via second diffusion-controlling means. Oxygen is pumped into the second processing zone by a second oxygen concentration adjustment pump element so as to burn the combustible gas component. The combustible gas component concentration is determined based on a value of current flowing through or voltage built up across the second oxygen concentration adjustment pump element.

The apparatus disclosed in the above-described patent publication employs a structure such that oxygen is pumped into the second processing zone by the second oxygen pump element in order to burn the combustible gas component on the electrode in the second processing zone. The oxygen concentration in the second processing zone is detected by the oxygen concentration cell element, and the second oxygen pump element is operated such that the detected electromotive force becomes constant. The concentration of the combustible gas component is detected on the basis of the pumping current of the second oxygen pump element. However, this structure has the following drawback. When the oxygen concentration changes as a result of combustion of the combustible gas component, this change is detected by the oxygen concentration cell element and is fed back to a control section for controlling the pumping current, so that the response in detecting the combustible gas component decreases accordingly.

Further, in the above disclosed apparatus, the oxygen concentration of the exhaust gas introduced into the first processing zone is reduced by the first oxygen concentration adjustment pump element to "a low value at which a combustible gas component is not substantially burned." According to the publication, the low value is not higher than $10^{-14}$ atm, preferably not higher than $10^{-16}$ atm, and is normally about $10^{-20}$ atm. However, when the oxygen concentration of the first processing zone is set at such a low value, there arises the following problem related to accuracy in measuring the combustible gas component concentration.

Specifically, an exhaust gas generally contains a fair amount of water vapor in addition to combustible gas components such as hydrocarbon, carbon monoxide, and hydrogen. Generally, the amount of water vapor varies according to operating conditions of an internal combustion engine. According to studies conducted by the inventors of the present invention, when the oxygen concentration of such an exhaust gas is reduced to the above-mentioned value, a portion of water vapor is decomposed into hydrogen and oxygen. The thus-generated oxygen is pumped out from the first processing zone by the first oxygen concentration adjustment pump element, whereas the thus-generated hydrogen is not pumped out, but introduced into the second processing zone, where the hydrogen induces combustion. If such a state occurs during measurement of a gas to be examined which mainly contains hydrocarbon as a combustible gas component, the accuracy in measuring hydrocarbon concentration is greatly affected by combustion of hydrogen generated through decomposition of water vapor. Notably, measurement examples disclosed in the above publication are all conducted under the condition that the water vapor concentration of the gas to be examined is constant, and do not refer to the influence of a variation in water vapor concentration on measurement of a combustible gas component concentration.

As disclosed in the above publication, a proton pump may be additionally used in order to pump out the thus-generation hydrogen from the first processing zone, so that only HC is selectively burned to thereby improve measurement accuracy. However, this method merely employs the proton pump as a means of last resort for coping with hydrogen generation associated with decomposition of water vapor. Addition of the proton pump makes a sensor structure and a sensor control mechanism complex, causing an increase in apparatus cost. Further, residual hydrogen which the proton pump has failed to pump out may induce a measurement error.

Also, the following problem is involved. With the recent tendency to tighten exhaust gas regulations for air pollution control, internal combustion engines such as gasoline engines, diesel engines, and like engines tend to shift to the lean-burn type in order to suppress generation of HC associated with incomplete combustion. An exhaust gas produced under lean-burn conditions has an oxygen concentration higher than that produced under stoichiometric or rich conditions. When the above-mentioned conventional apparatus is applied to such an exhaust gas, an oxygen concentration adjustment pump element carries a significant burden in order to reduce the oxygen concentration to the above-mentioned low value. As a result, the service life of the oxygen concentration adjustment pump element is shortened. Further, since the operating power of the oxygen concentration adjustment pump element must be increased, a peripheral control circuit must be of high output, causing an increase in apparatus cost.

SUMMARY OF THE INVENTION

A first object of the present invention is to provide a gas sensor which can detect the concentration of a combustible gas component in a measurement gas, such as exhaust gas, with high accuracy even when the oxygen concentration of the measurement gas or the element temperature changes and which has an excellent response in detecting the combustible gas component, as well as to provide a gas sensor system using the gas sensor. An second object of the present invention is to provide a gas sensor in which accuracy in measuring a combustible gas component concentration is less susceptible to decomposition of water vapor and which is suitably applicable to lean-burn conditions, as well as to provide a gas sensor system using the gas sensor.

The gas sensor of the present invention has the following constituent features.
1. First processing space: Isolated from surroundings. A measurement gas is introduced into the first processing space via a first gas passage.
2. Second processing space: Isolated from surroundings. A gas contained in the first processing space is introduced into the second processing space via a second gas passage.
3. Oxygen concentration detection element: Adapted to measure the oxygen concentration of a gas contained in the first processing space.
4. Oxygen concentration adjustment pump element: Formed of an oxygen-ion-conductive solid electrolyte and having electrodes formed on both surfaces thereof. The oxygen concentration adjustment pump element pumps out oxygen from the first processing space or pumps oxygen into the first processing space so as to adjust to a predetermined level the oxygen concentration of the measurement gas introduced into the first processing space, which is detected by the oxygen concentration detection element.
5. Oxidation catalyst section: Adapted to accelerate combustion of a combustible gas component contained in the gas which has been introduced into the second processing space from the first processing space via the second gas passage.
6. Measurement-purpose-oxygen supply pump element: Formed of an oxygen-ion-conductive solid electrolyte and having electrodes formed on both surfaces thereof. One of the electrodes is disposed to be exposed to the second processing space. A voltage is applied between the electrodes in order to pump into the second processing space a constant amount of oxygen used for measurement of the combustible gas component contained in the measurement gas.
7. Combustible gas component concentration detection element: Formed of an oxygen-ion-conductive solid electrolyte and having electrodes formed on both surfaces thereof. One of the electrodes is disposed to be exposed to the second processing space. A constant voltage is applied between the electrodes in a direction for pumping out oxygen from the second processing space (i.e., a direction such that the electrode facing the second processing space become negative), so that a current output from the combustible gas component concentration detection element varies according to the amount of oxygen consumed by combustion of the combustible gas component contained in the gas introduced from the first processing space into the second processing space to thereby provide information regarding a detected concentration of the combustible gas component of the measurement gas.

A gas sensor system of the present invention has the following constituent features.
(A) Gas sensor: Configured to have the following constituent features.
1. First processing space: Isolated from surroundings. A measurement gas is introduced into the first processing space via a first gas passage.
2. Second processing space: Isolated from surroundings. A gas contained in the first processing space is introduced into the second processing space via a second gas passage.
3. Oxygen concentration detection element: Adapted to measure the oxygen concentration of a gas contained in the first processing space.
4. Oxygen concentration adjustment pump element: Formed of an oxygen-ion-conductive solid electrolyte and having electrodes formed on both surfaces thereof. The oxygen concentration adjustment pump element pumps out oxygen from the first processing space or pumps oxygen into the first processing space.
5. Oxidation catalyst section: Adapted to accelerate combustion of a combustible gas component contained in the gas which has been introduced into the second processing space from the first processing space via the second gas passage.
6. Measurement-purpose-oxygen supply pump element: Formed of an oxygen-ion-conductive solid electrolyte and having electrodes formed on both surfaces thereof. One of the electrodes is disposed to be exposed to the second processing space. A voltage is applied between the electrodes in order to pump into the second processing space a constant amount of oxygen used for measurement of the combustible gas component contained in the measurement gas.
7. Combustible gas component concentration detection element: Formed of an oxygen-ion-conductive solid electrolyte and having electrodes formed on both surfaces thereof. One of the electrodes is disposed to be exposed to the second processing space. A constant voltage is applied between the electrodes in a direction for pumping out oxygen from the second processing space, so that a current output from the combustible gas component concentration detection element varies according to the amount of oxygen consumed by combustion of the combustible gas component contained in the gas introduced from the first processing space into the second processing space to thereby provide information regarding a detected concentration of the combustible gas component of the measurement gas.
(B) Oxygen pump operation control means: Adapted to control the oxygen concentration adjustment pump element so as to reduce to a predetermined level the oxygen concentration of the measurement gas introduced into the first processing space, which is detected by the oxygen concentration detection element.
(C) Voltage application means: Adapted to apply a voltage to the combustible gas component concentration detection element.
(D) Pumping current supply means: Adapted to cause pumping current to flow between the electrodes of the measurement-purpose-oxygen supply pump element in order to pump in oxygen for measurement.

The gas sensor and the gas sensor system of the present invention sense a combustible gas component selected singly or in combination from the group consisting of, for example, hydrocarbon (HC), carbon monoxide, and hydrogen.

In the configuration described above, the oxygen concentration of the measurement gas contained in the first processing space is adjusted to a predetermined level through operation of the oxygen concentration adjustment pump element. The thus-treated gas is introduced into the second processing space, where a combustible gas component undergoes combustion through the assistance of the oxidation catalyst section. The combustible gas component concentration detection element, to which a constant voltage is applied, varies its output current according to oxygen consumption associated with the above-mentioned combustion of the combustible gas component. Thus, on the basis of the output current, information regarding the combustible gas component concentration of the original measurement gas can be determined. Since the oxygen concentration of the measurement gas detected by the oxygen concentration detection element is adjusted to a predetermined level before the gas is measured for a combustible gas component concentration, an output from the combustible gas component concentration detection element is less susceptible to the original oxygen concentration of the measurement gas. Thus, the relationship between an output current of the combustible gas component concentration detection element and the combustible gas component concentration of the measurement gas exhibits good linearity.

In the sensor of the present invention, oxygen required for burning the combustible gas component in the second processing space is supplemented by the measurement-purpose-oxygen supply pump element. Although the measurement-purpose-oxygen supply pump element seems to have a role similar to that of the second oxygen pump element of the apparatus disclosed in the above-described patent publication, the measurement-purpose-oxygen supply pump element greatly differs from the second oxygen pump element as described below. That is, in the apparatus disclosed in the patent publication, the second oxygen pump element is subjected to feedback control performed on the basis of information which is output from the oxygen concentration cell element and represents the detected oxygen concentration, and the pump current of the second oxygen pump element is detected as a combustible gas component concentration. By contrast, in the sensor of the present invention, the measurement-purpose-oxygen supply pump element supplies oxygen to the second processing space in only an amount necessary and sufficient for burning the combustible gas component, and the concentration of the combustible gas component is detected on the basis of information representing the current flowing through the combustible gas component concentration detection element. That is, unlike the apparatus disclosed in the patent publication, the sensor of the present invention does not employ a feedback system. Therefore, a variation in the concentration of the combustible gas component is directly reflected in a variation in the current of the combustible gas component concentration detection element, so that a high detection response is obtained. Thus, the above-described first object is achieved.

The rate of supply of oxygen to the second processing space is preferably maintained constant in view of accurate detection of the combustible gas component concentration. That is, the current flowing through the measurement-purpose-oxygen supply pump element is preferably maintained constant. When the combustible gas component concentration increases and a portion of the combustible gas component remains unburned, the measurement accuracy decreases. Therefore, in order to sufficiently promote combustion of the combustible gas component, the rate of supply of oxygen to the second processing space (i.e., the current flowing through the measurement-purpose-oxygen supply pump element) must be set to a proper value in accordance with the highest combustible gas component concentration to be detected. In this case, in order to guarantee supply of oxygen necessary for combustion of the combustible gas component in the second processing space, oxygen is preferably supplied to the second processing space in a slightly excess amount; i.e., the current flowing through the measurement-purpose-oxygen supply pump element is set to a slightly higher level, such that the current always flows through the combustible gas component concentration detection element in a direction for pumping out oxygen. The constant current supplied to the measurement-purpose-oxygen supply pump element preferably falls within a range of 20 to 50 $\mu$A in an exemplary case where a concentration of methane is to be measured up to 1000 ppm.

Further, the constant voltage applied to the combustible gas component concentration detection element is adjusted such that the partial pressure falls within a range in which there occurs substantially no decomposition of nitrogen oxides in the gas introduced in the second processing space. This adjustment prevents a decrease in the accuracy in detecting the combustible gas component concentration that results from oxygen generated from decomposition of nitrogen oxides.

In the gas sensor of the present invention, the oxygen concentration adjustment pump element may be operated so as to adjust the oxygen concentration of the measurement gas introduced in the first processing space, which concentration is detected by the oxygen concentration detection element, within a range in which there occurs substantially no decomposition of water vapor contained in the measurement gas. In this case, the oxygen pump operation control means of the gas sensor system controls the operation of the oxygen concentration adjustment pump element such that the oxygen concentration of the measurement gas introduced in the first processing space, which concentration is detected by the oxygen concentration detection element, is adjusted within a range in which there occurs substantially no decomposition of water vapor contained in the measurement gas.

As described above, by substantially suppressing hydrogen generation due to decomposition of water vapor through oxygen concentration adjustment, there can be prevented an impairment in accuracy in measuring a combustible gas component concentration which would otherwise result from combustion of the generated hydrogen. Also, the gas sensor and the gas sensor system of the present invention exhibit excellent selectivity toward HC, particularly methane, and thus can measure a methane concentration more accurately than do conventional gas sensors. Thus, the second object of the present invention is accomplished.

When a measurement gas contains carbon dioxide and the carbon dioxide is decomposed, carbon monoxide—which is a combustible gas component—is generated as in the case of water vapor from which hydrogen is generated. Combustion of the thus-generated carbon monoxide may lower the accuracy in detecting the combustible gas component. In such a case, it is further preferred that the oxygen concentration adjustment pump element adjust the oxygen concentration of the measurement gas introduced into the first processing space, which is detected by the oxygen concentration detection sensor, such that the oxygen concentration falls within such a range that a reaction of decomposing carbon dioxide is not substantially initiated. Since the oxygen concentration at which decomposition of carbon dioxide occurs is generally lower than the oxygen concentration at which decomposition of water vapor occurs, the decomposition of carbon dioxide is concurrently prevented through employment of the condition of oxygen concentration that prevents decomposition of water vapor.

The oxygen concentration adjustment pump element may be operated such that the oxygen concentration of the measurement gas introduced into the first processing space is adjusted within the range of $10^{-12}$ atm to $10^{-6}$ atm. In this case, the oxygen pump operation control means of the gas sensor system controls the operation of the oxygen concentration adjustment pump element such that the oxygen concentration of the measurement gas introduced into the first processing space, which concentration is detected by the oxygen concentration detection element, is adjusted within the range of $10^{-12}$ atm to $10^{-6}$ atm.

In the above-mentioned configuration, the oxygen concentration of the first processing space achieved through operation of the oxygen concentration adjustment pump element is adjusted within the above range, thereby suppressing decomposition of water vapor and thus improving the sensing accuracy of the gas sensor or the gas sensor system. Since an oxygen concentration to be achieved through adjustment is far higher than a conventionally required oxygen concentration of $10^{-20}$ atm to $10^{-14}$ atm, the oxygen concentration adjustment pump element carries a smaller burden even in measurement, for example, under lean-burn conditions. Thus, the service life of the oxygen concentration adjustment pump element is expanded. Also, a required power to operate the oxygen concentration adjustment pump element is not very high, and a control circuit and other peripheral devices can be formed at low cost. Also, in this case, the oxygen concentration adjustment pump element (or the oxygen pump control means) is preferably configured such that the oxygen concentration of a measurement gas introduced into the first processing space, which is detected by the oxygen concentration detection element, is adjusted such that the oxygen concentration falls within such a range that a reaction of decomposing water vapor contained in the measurement gas is not substantially initiated. In the gas sensor and the gas sensor system described above, in order to further effectively prevent decomposition of water vapor, the oxygen concentration adjustment pump element is preferably operated such that the oxygen concentration of the first processing space is adjusted to a value at which a portion of a combustible gas component is burned in the first processing space while a first electrode serves as oxidation catalyst.

Further, when a detection selectivity toward hydrocarbon (especially, methane or the like having a relatively low combustion activity) is required to be improved, the oxygen concentration within the first processing space detected by the oxygen concentration detection element is preferably adjusted such that the oxygen concentration falls within such a range that a component (e.g., carbon monoxide, hydrogen, ammonia) having a higher combustion activity than does hydrocarbon to be detected is burned more readily than is hydrocarbon to be detected. This adjustment improves the detection selectivity toward hydrocarbon (e.g. methane). The oxygen concentration range varies depending on the combustion catalytic activity of the first and fourth electrodes, which will be described later, toward various combustible gas components. However, the oxygen concentration range is $10^{-12}$–$10^{-6}$ atm, preferably $10^{-11}$–$10^{-9}$ atm.

When the oxygen concentration of a measurement gas introduced into the first processing space becomes less than $10^{-12}$ atm, decomposition of water vapor, if contained, becomes conspicuous. As a result, hydrogen generated through decomposition of water vapor may significantly impair accuracy in measuring a combustible gas component concentration. By contrast, when the oxygen concentration of the first processing space is in excess of $10^{-6}$ atm, combustion of a combustible gas component becomes conspicuous in the first processing space. Accordingly, the combustible gas component concentration of a gas introduced into the second processing space becomes small with a potential failure to attain a predetermined measurement accuracy. More preferably, the oxygen concentration of the first processing space is adjusted to a value of $10^{-11}$ atm to $10^{-9}$ atm.

For example, when the gas sensor is set at a working temperature of 650° C. to 700° C. and the water vapor concentration of a measurement gas varies within a range of about 5% to 15%, oxygen that maintains equilibrium with water vapor and hydrogen has a minimum partial pressure of about $10^{-12}$ atm. When the partial pressure of oxygen drops below the minimum value, decomposition of water vapor progresses, affecting accuracy in measuring a combustible gas component concentration. Therefore, in this case, the oxygen concentration of the first processing space is preferably set to a value greater than the above minimum partial pressure of oxygen.

In this specification, unless specifically described otherwise, the oxygen concentration within the first processing space means the oxygen concentration detected by the oxygen concentration detection element. For example, when a part of a combustible gas component contained in a measurement gas burns and consumes oxygen, the oxygen concentration detected by the oxygen concentration detection element is not necessarily equal to the oxygen concentration before the consumption of oxygen due to combustion. Also, the oxygen concentration may vary at locations within the first processing space due to existence of a porous electrode that is disposed to face the first processing space and catalyzes combustion of a combustible gas component, or due to oxygen pumping of the oxygen concentration adjustment pump element. In this case as well, the oxygen concentration detected by the oxygen concentration detection element is considered to represent the oxygen concentration within the first processing space.

In the gas sensor (and the gas sensor system) described above, at least either the first gas passage for introducing a measurement gas into the first processing space from outside or the second gas passage for establishing communication between the first processing space and the second processing space may be configured so as to serve as a diffusion-controlling passage for permitting gas flow at a constant diffusion resistance. This feature suppresses compositional variation of a gas introduced into the first or second processing space to a small degree of variations for a constant period of time determined by the diffusion resistance of the passage even under varying measurement gas concentration of an atmosphere subjected to measurement. Thus, accuracy in measuring a combustible gas composition concentration can be improved. Specifically, the diffusion-controlling passage may assume the form of small holes or slits or may be formed of any of various throttling mechanisms or porous metals or ceramics having communicating pores formed therein.

In the gas sensor and the gas sensor system described above, the oxygen concentration detection element may be an oxygen concentration cell element. The oxygen concentration cell element is formed of an oxygen-ion-conductive solid electrolyte and having electrodes formed on both surfaces thereof. One of the electrodes is disposed in such a manner as to be exposed to the first processing space. In this case, each of the electrode (second electrode) of the combustible gas component concentration detection element exposed to the second processing space, the electrode (third electrode) of the measurement-purpose-oxygen supply pump element exposed to the second processing space, the electrode (first electrode) of the oxygen concentration cell element exposed to the first processing space, and the electrode (fourth electrode) of the oxygen concentration adjustment pump element exposed to the first processing space may assume a form of a porous electrode having oxygen molecule dissociating capability, and at least one of the second and third electrodes may have catalytic activity for oxidation of the combustible gas component contained in the measurement gas and serves as the oxidation catalyst section. In this case, the oxidation catalytic activities of the above-described electrodes (first through fourth electrodes) are adjusted such that an amount of oxygen consumed in the second processing space due to combustion of the combustible gas component becomes greater than that in the first processing space. Thus, at least a portion of a residual combustible gas component which has not been burned in the first processing space can be reliably burned in the second processing space, thereby improving sensor sensitivity. Further, since the electrode (second electrode) of the combustible gas component concentration detection element exposed to the second processing space also serves as an oxidation catalyst section, the structure of the gas sensor or the gas sensor system is further simplified.

In view of stabilization of a sensor output, it is preferred that the electrode (second electrode) of the combustible gas component concentration detection element exposed to the second processing space be positioned in such a manner as not to interfere with the second gas passage. When the electrode interferes with the second gas passage, combustion of a combustible gas component may be initiated before equilibrium is established between a gas which is newly introduced into the second processing space from the first processing space and a gas which is already present in the second processing space. When the positional interference is avoided, such a phenomenon is less likely to occur, thereby stabilizing a sensor output.

When a gas component to be measured is CO or HC, an electrode having higher catalytic activity for oxidation may be formed of Pt, Pd, Rh, a Pt alloy, a Pd alloy, an Rh alloy, a Pt—Rh alloy, an Rh—Pd alloy, a Pd—Ag alloy, or a like metal (hereinafter these metals are referred to as metals of a high-activity metal group). An electrode having lower catalytic activity for oxidation may be formed of Au, Ni, Ag, an Au alloy, an Ni alloy, an Ag alloy, a Pt—Pd alloy, a Pt—Au alloy, a Pt—Ni alloy, a Pt—Ag alloy, an Ag—Pd alloy, an Au—Pd alloy, or a like metal (hereinafter these metals are referred to as metals of a low-activity metal group). When a $ZrO_2$ solid electrolyte, which will be described later, is used as an oxygen-ion-conductive solid electrolyte that constitutes a main portion of the oxygen concentration adjustment pump element, that of the oxygen concentration cell element, or that of the combustible gas component concentration detection element, a metal of the low-activity metal group to be selected is preferably the one that can be fired with the $ZrO_2$ solid electrolyte (firing temperature: 1450° C. to 1500° C.), in view of improvement in sensor-manufacturing efficiency. For example, when a Pt—Au alloy is used, the Au contents thereof may be 0.1% to 3% by weight. When the Au content is less than 0.1% by weight, an electrode formed of the alloy may have an excessively high catalytic activity for oxidation.

In the gas sensor of the present invention, a more preferable result is obtained through employment of an electrode having the following structure. Specifically, the oxygen concentration adjustment pump element is formed of an oxygen-ion-conductive solid electrolyte and has electrodes formed on both surfaces thereof, and one of the electrodes (hereinafter referred to as the "fourth electrode") is disposed in such a manner as to be exposed to the first processing space. When a component to be detected is CO or HC, the fourth electrode is composed of two layers, i.e., a porous main electrode layer and a porous surface electrode layer. The porous main electrode layer is made of Pt—Au alloy or Pt. The porous surface electrode layer covers the main electrode layer to thereby form a surface layer portion of the fourth electrode. The surface electrode layer is made of a material selected from the group consisting of a metal containing Au or Ag as a main component, Pt—Au alloy, Au—Pd alloy, Pt—Ag alloy, and Pt—Ni alloy (hereinafter collectively referred to as "inactive metal"). In this specification, the term "X-Y alloy" means an alloy in which a metal component having a highest content by weight is X, and a metal component having a second highest content by weight is Y, and may be an X-Y binary system alloy or a higher-order system alloy containing X, Y, and other alloy components.

Materials for the electrodes of the oxygen concentration cell element or the oxygen concentration adjustment pump element must have a sufficient catalytic activity for dissociation and recombination of oxygen molecules. Pt single metal, for example, is an excellent material in this point. However, if this material is used for the electrode exposed to the first processing space, the material has an extremely high combustion catalytic activity toward a combustion gas component. Therefore, the catalytic activity must be decreased slightly. For example, as conventionally practiced, Au, whose combustion catalytic activity is low, is mixed to Pt up to about 20 wt. %, thereby forming a Pt—Au alloy. However, when the Au content increases, a drastic decrease in the activity for dissociating oxygen molecules occurs concurrently with a decrease in the catalytic activity for combustion of a combustible gas component. Therefore, these two catalytic activities are difficult to balance.

This problem can be solved through employment of the above-described multilayer electrode, in which the surface of the porous main electrode layer formed of Pt—Au alloy or Pt having a high activity for dissociating oxygen molecules is covered with the porous surface electrode layer formed of an inactive metal having a low combustion catalytic activity toward a combustible gas component. This structure enables convenient adjustment to decrease the combustion catalytic activity toward a combustible gas component to a possible extent, while maintaining a sufficient level of oxygen molecule dissociation activity.

In the present invention, the surface electrode layer is preferably formed of an Au-containing porous metal that has a considerably low combustion catalytic activity toward CO or HC and some degree of catalytic activity for dissociation and recombination of oxygen molecules. However, there may alternatively be used a porous metal containing Ag as a main component, a porous Pt—Au alloy (Au content: 5 wt. % or more), a porous Pt—Pb alloy (Pb content: 1 wt. % or more), a porous Pt—Ag alloy (Ag content: 1 wt. % or more), a porous Pt—Ni alloy (Ni content: 1 wt. % or more), and the like.

The surface electrode layer and the main electrode layer may be arranged such that these layers come into indirect contact with each other via one or more other layers.

However, employment of a two-layer structure comprising the main electrode layer and the surface electrode layer simplifies the manufacturing process. In this case, when the surface electrode layer is formed of an Au-containing porous metal that contains Au as a main component, there can be obtained the remarkable effect of suppressing the combustion catalytic activity toward a combustible gas component, while there is maintained a sufficient level of oxygen molecule dissociation activity.

The above-described multilayer electrode is advantageously employed for the fourth electrode of the oxygen concentration adjustment pump element which is not required to have a sharp response to oxygen concentration. It is not impossible to use the above-described multilayer electrode for the first electrode of the oxygen concentration cell element. However, in order to further improve the accuracy in detecting the oxygen concentration within the first processing space by use of the oxygen concentration cell element, the first electrode is preferably formed of Pt, Pt—Au alloy, or Pt—Ag alloy. In this case, since combustion of a combustible gas component that is caused by the first electrode within the first processing space can be suppressed by making the area of the first electrode smaller than that of the fourth electrode, the loss caused by the combustion of the combustible gas component within the first processing space can be decreased, so that the sensor sensitivity can be increased further.

When Pt—Au alloy or Pt—Ag alloy is used for the first electrode, Au or Ag is added in order to suppress the combustion catalytic activity toward CO or HC. In this case, when the Au or Ag content exceeds 1 wt. %, the oxygen molecule dissociation activity decreases excessively, resulting in a deterioration of the oxygen concentration detection performance. By contrast, when the Au or Ag content is less than 0.1 Wt. %, almost no effect of suppressing the combustion catalytic activity is expected. Au and Ag may be added together into Pt such that their total content does not exceed 1 wt. %.

When a detection selectivity for hydrocarbon among various combustible gas components must be improved, a component having a higher combustion activity than does hydrocarbon to be detected is preferably burned more readily than is hydrocarbon to be detected. In this case, as described above, the oxygen concentration within the first processing space detected by the oxygen concentration detection element is adjusted. Further, the combustion catalytic activity of the first electrode or the fourth electrode exposed to the first processing space and the temperature within the first processing space are important factors in improving the detection selectivity. When the fourth electrode is formed of the above-described multilayer electrode having a relatively low combustion catalytic activity and the first electrode is formed of Pt or Pt alloy having a high combustion catalytic activity, a hydrocarbon component (e.g., methane) having a slightly low combustion activity does not burn much, while components such as carbon monoxide, hydrogen, ammonia, which have a higher combustion activity, burn readily on the first electrode. As a result, there is created an environment convenient for selective detection of hydrocarbon components. When the temperature within the first processing space increases, combustion reaction proceeds easily, and a difference in combustion catalytic activity is not produced so much between electrodes of different materials. These are disadvantageous for selective detection of hydrocarbon components. However, when the fourth electrode has the above-described multilayer structure, a considerably large difference in catalytic activity between the fourth electrode and the first electrode formed of Pt or the like is produced even at considerably high temperatures (e.g. 700–800° C.), so that selective detection of hydrocarbon components can be performed effectively.

When the fourth electrode is formed into the above-described multilayer structure, the gas sensor of the present invention can be manufactured in accordance with the method comprising the following steps.

(1) A substrate electrode layer forming step in which a substrate electrode pattern containing an unfired layer of material powder for the main electrode layer of the fourth electrode (hereinafter referred to as the "unfired main electrode layer") is formed on an unfired compact of the oxygen-ion-conductive solid electrolyte layer contained in the oxygen concentration adjustment pump element (hereinafter referred to as the "unfired solid electrolyte compact"), and the unfired main electrode layer is integrally fired with the unfired solid electrolyte compact in order to form on the oxygen-ion-conductive solid electrolyte layer a substrate electrode layer containing the main electrode layer.

(2) A surface electrode layer forming step in which a layer of material powder for the surface electrode layer is formed on the substrate electrode layer, and is subjected to a secondary firing at a temperature lower than that in the integral firing to thereby form the surface electrode layer. The layer of material power may be formed through, for example, application of paste of the material powder onto the main electrode layer.

Since the substrate electrode layer containing the main electrode layer is formed of a high-melting point metal such as Pt or a Pt—Au or Pt—Ag alloy having the above-described composition, the substrate electrode layer can be fired concurrently with solid electrolyte ceramic, such as zirconia, that constitutes the main portion of each element. However, when the surface electrode layer is formed of an Au-containing metal, which has a low melting point, maintaining the porous state of the substrate electrode layer becomes impossible when it is fired together with solid electrolyte ceramic. In addition, Au diffuses into the substrate electrode layer, and therefore it becomes impossible to achieve the effect of suppressing the combustion catalytic activity. In order to solve this problem, there is employed the above-described process in which the surface electrode layer is subjected to secondary firing at a temperature lower than that for the integral firing of the substrate electrode layer and the solid electrolyte layer in order to bond the surface electrode layer to the substrate electrode layer through baking. Thus, a multilayer electrode having a desired performance is obtained.

The components (e.g., Au) of the surface electrode layer may diffuse into the main electrode layer during the secondary firing or when the sensor is used at high temperature. For example, even if the main electrode layer is substantially formed of Pt, Au may diffuse from the surface electrode layer into the main electrode layer so that Au constituting the main electrode layer is converted into Pt—Au alloy. If the diffusion of the material of the surface electrode layer into the main electrode layer proceeds excessively, the thickness of the surface electrode layer becomes insufficient, or in an extreme case, the surface electrode layer disappears. For example, when it is desired that the surface electrode layer be formed mainly of Au and the main electrode layer be formed mainly of Pt, the temperature for secondary firing is preferably set to about 800–1050° C. in order to prevent excessive diffusion of Au into the main electrode layer. When the secondary firing temperature is less than 800° C., firing of the surface electrode layer becomes insufficient with a possible result that delamination of the surface electrode layer occurs due to insufficient closeness of contact. By contrast, when the secondary firing temperature is greater than 1050° C., the thickness of the surface electrode layer becomes insufficient due to diffusion of the Au component, or firing proceeds excessively, so that the porous structure is lost. In this case, the oxygen permeability that the porous electrode must have becomes difficult to maintain. When Au is mixed in the constituent metal of the main electrode layer in an amount of about 3–10 wt. % from the beginning, the diffusion of Au from the surface electrode layer into the main electrode layer can be suppressed because the limit of solid solution of Au into Pt is relatively small (about 5 wt. % at 800° C.). Thus, the drawbacks such as a reduction in thickness of the surface electrode layer can be effectively avoided.

The manufacturing method comprising the above-described secondary firing step can be performed efficiently, when the gas sensor of the present invention is constructed such that a pump cell unit including the oxygen concentration adjustment pump element is formed separately from a sensor cell unit including the oxygen concentration detection element, the second processing space, and the combustible gas component concentration detection element; and the pump cell unit and the sensor cell unit are joined and integrated with each other through use of a bonding material. In this case, the pump cell unit is manufactured through firing such that the substrate electrode layer is formed without formation of the surface electrode layer; the secondary firing is performed in order to form the surface electrode layer on the substrate electrode layer of the pump cell unit; and the pump cell unit is integrated with the sensor cell unit, which has been separately manufactured through firing. Thus, the gas sensor is obtained. Preferably, a pump-cell-side fitting portion is formed in the pump cell unit, and a sensor-cell-side fitting portion to be engaged with the pump-cell-side fitting portion is formed in the sensor cell unit. In this case, positioning during joining can be easily performed through engagement between the pump-cell-side fitting portion and the sensor-cell-side fitting portion. Thus, manufacturing efficiency of the sensor can be improved.

In the gas sensor of the present invention, the oxygen concentration cell element or the combustible gas component concentration detection element may be formed of an oxygen-ion-conductive solid electrolyte composed mainly of $ZrO_2$ ($ZrO_2$ solid electrolyte). In the oxygen concentration cell element formed of a $ZrO_2$ solid electrolyte, one electrode is in contact with a gas to be measured, which gas contains oxygen and a combustible gas component, while the other electrode is in contact with a reference atmosphere having a constant oxygen concentration. An electromotive force of the oxygen concentration cell element varies abruptly when a gas composition falls outside a stoichiometric composition in which oxygen and a combustible gas component are present in a proper ratio so that they react with each other completely. When an ordinary gasoline engine or diesel engine is operated under lean-burn conditions, a measurement gas emitted from the engine contains combustible gas components in a total concentration of about 0 to 1000 ppmC (ppmC: parts per million represented with carbon equivalent). A measurement gas having such a combustible gas component concentration is introduced into the first processing space, and the oxygen concentration of the introduced measurement gas is adjusted to $10^{-6}$ atm (preferably $10^{-9}$ atm) or lower, as mentioned previously. As a result, a gas introduced into the second processing space from the first processing space has a stoichiometric composition or a composition shifted slightly toward a rich condition. Thus, an output from the combustible gas component concentration detection element is increased, thereby improving the sensitivity of the gas sensor.

When the oxygen concentration adjustment pump element, the oxygen concentration cell element, and the combustible gas component concentration detection element are formed of the $ZrO_2$ solid electrolyte mentioned above, a heating element may be provided for heating the elements to a predetermined working temperature. The working temperature may be set to 650° C. to 800° C. When the working temperature is in excess of 800° C., an output current value of the combustible gas component concentration detection element becomes excessively low, causing impairment in the sensitivity of the gas sensor. This is conceivably because most of a combustible gas component, such as an HC component, contained in a measurement gas is burned in the first processing space due to the working temperature being high. By contrast, when the working temperature is lower than 650° C., the internal resistance of the oxygen concentration adjustment pump element increases, causing unstable operation. As a result, accuracy in measuring a combustible gas component may be impaired.

In the gas sensor and the gas sensor system of the present invention, the oxygen concentration detection element may be an oxygen concentration cell element formed of an oxygen-ion-conductive solid electrolyte and having porous metal electrodes formed on both surfaces thereof. One of the electrodes (hereinafter referred to as the "first electrode") may serve as a detection-side electrode disposed in such a manner as to be exposed to said first processing space, and the other electrode may serve as an oxygen reference electrode. In this case, the oxygen reference electrode of the oxygen concentration detection element is used as the electrode of the combustible gas component concentration detection element opposite the electrode (hereinafter referred to as the "second electrode") thereof exposed to the second processing space. This arrangement enables the oxygen concentration detection element and the combustible gas component concentration detection element to share the oxygen reference electrode, thereby implementing a compact sensor.

More specifically, the first processing space and the second processing space may be arranged with a partition wall, formed of an oxygen-ion-conductive solid electrolyte, disposed therebetween. In this case, the second gas passage is formed in the partition wall so as to establish communication between the first processing space and the second processing space. An oxygen reference electrode is embedded in the partition wall at a thicknesswise intermediate portion. The first electrode is formed on the partition wall in such a manner as to be exposed to the first processing space. The oxygen concentration cell element is constituted by the first electrode, the oxygen reference electrode, and a portion of the partition wall interposed between the first electrode and the oxygen reference electrode. Also, the second electrode is formed on the partition wall in such a manner as to be exposed to the second processing space. The combustible gas component concentration detection element is constituted by the second electrode, the oxygen reference electrode, and a portion of the partition wall interposed between the second electrode and the oxygen reference electrode. The oxygen concentration adjustment pump element is arranged opposite to the partition wall with the first processing space disposed therebetween. This arrangement enables all the elements to be formed in a laminated configuration, to thereby make the sensor more compact.

The oxygen reference electrode of the oxygen concentration cell element may be a self-generation-type oxygen reference electrode. That is, a small pumping current is caused to flow between the detection-side electrode and the oxygen reference electrode of the oxygen concentration cell element in a direction such that oxygen is pumped toward the oxygen reference electrode, so that the thus-pumped oxygen establishes a predetermined reference oxygen concentration within the oxygen reference electrode. Thus, the oxygen concentration at the oxygen reference electrode side can be stabilized, so that oxygen concentration can be measured with higher accuracy.

When the oxygen concentration detection element and the combustible gas component concentration detection element shares the oxygen reference electrode, and the oxygen reference electrode is configured to serve as the self-generation-type oxygen reference electrode, a current limit circuit is preferably provided in order to prevent an amount of current flowing through the combustible gas component concentration detection element between the second electrode and the oxygen reference electrode from falling outside a predetermined range. If such an excessive current flows from the oxygen reference electrode to the second electrode, a large amount of oxygen flows toward the oxygen reference electrode, so that the internal pressure of the oxygen reference electrode becomes excessively high, resulting in occurrence of problems such as breakage of the electrode. Such problems can be avoided through provision of the above-described current limit circuit.

The current limit circuit may be configured to prevent an amount of current flowing from the oxygen reference electrode to the second electrode from exceeding a predetermined value. The fact that current flows from the second electrode to the oxygen reference electrode means that oxygen flows out from the oxygen reference electrode toward the second electrode, because the oxygen-ion-conductive solid electrolyte is present therebetween. When such a current flows excessively, a large amount of oxygen flows out from the oxygen reference electrode, so that the oxygen reference electrode becomes difficult to secure a necessary oxygen concentration. As a result, it becomes impossible to operate the oxygen concentration cell element properly or normally, or to control the oxygen concentration in the first processing space, resulting in a decreased detection accuracy of the sensor. This drawback can be avoided through provision of the above-described current limit circuit.

Preferably, at least either the oxygen reference electrode or the second electrode is formed in or on the partition wall at such a position as not to interfere with the second gas passage. More preferably, both of them are positioned in such a manner as not to interfere with the second gas passage. Positioning the second electrode in such a manner yields the aforementioned advantage. Also, positioning the oxygen reference electrode in such a manner prevents leakage of oxygen from the oxygen reference electrode through the second gas passage, thereby stabilizing an oxygen reference concentration and thus stabilizing a sensor output indicative of a combustible gas component concentration.

In the above gas sensor, the current flowing through the oxygen pump element, i.e., an oxygen pump current, varies according to the oxygen concentration of a measurement gas. Accordingly, the oxygen pump current reflects the oxygen concentration of the measurement gas. Therefore, in the gas sensor system of the present invention, there may be provided correction means for correcting an output of the combustible gas component concentration detection element based on the oxygen concentration of a measurement gas reflected in the oxygen pump current. That is, as mentioned previously, the gas sensor system of the present invention is characterized by having less susceptibility to the oxygen concentration of a measurement gas. Nevertheless, when the oxygen concentration causes variations in the output, such variations can be corrected by the correction means, thereby further improving accuracy in measuring a combustible gas concentration.

Specifically, the correction means may include storage means and correction value determination means. The storage means stores information regarding the relation between an output current of the combustible gas component concentration detection element and a combustible gas component concentration, relative to various values of oxygen concentration (or values of oxygen pump current). The correction value determination means determines a corrected output current (or a corresponding combustible gas component concentration) based on an output current of the combustible gas component concentration detection element and the above information. Thus, a detected combustible gas component concentration can be corrected in a rational manner.

BRIEF DESCRIPTION OF THE DRAWINGS

Embodiments of the present invention will now be described, by way of example only, with reference to the accompanying drawings, in which:

FIG. 7 gives perspective views showing a method of manufacturing the pump cell unit of the gas sensor of FIG. 1;

Figure 1A:
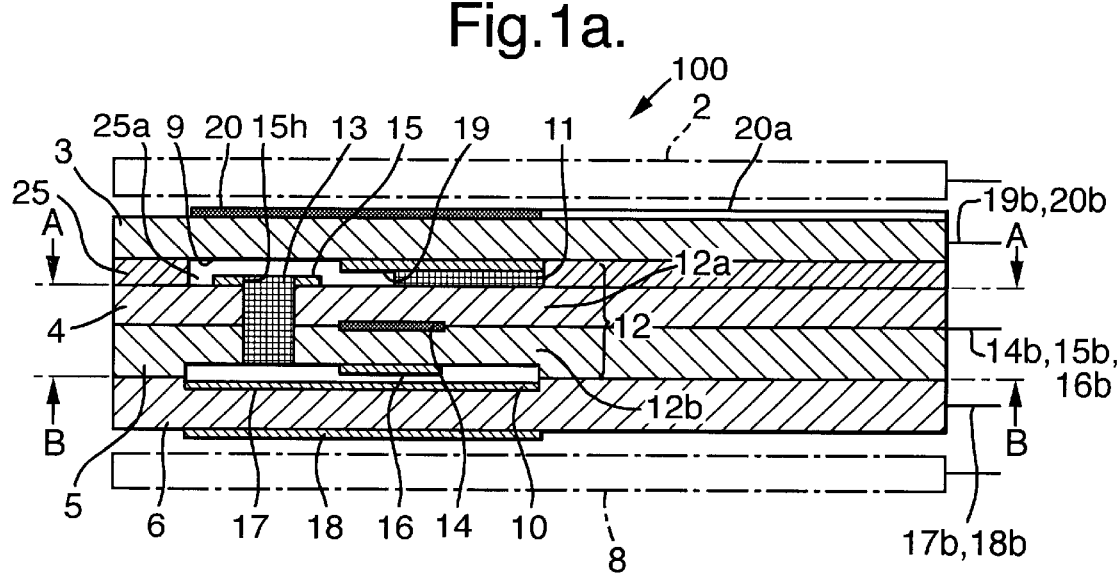
FIG. 1 is a sectional front view showing an example of a gas sensor of the present invention, a sectional view taken along line A—A, and a sectional view taken along line B—B.

In the drawings reference numerals are used to identify parts as follows:
1: gas sensor
2: first heater
3: oxygen concentration adjustment pump element
4: oxygen concentration cell element (oxygen concentration detection element)
5: combustible gas component concentration detection element
6: measurement-purpose-oxygen supply pump element
8: second heater
9: first processing space
10: second processing space
11: first gas passage
12: partition wall
13: second gas passage
14: oxygen reference electrode
15: first electrode
16: second electrode (oxidation catalyst section)
17: third electrode (oxidation catalyst section)
19: fourth electrode
50: gas sensor system
51: peripheral circuit
52: microprocessor
53: CPU (correction means)
54: RAM
55: ROM
56: I/O port
57: differential amplifier (oxygen pump operation control means)
71: constant DC-voltage power source (voltage application means)
80: constant current power source (pumping current supply means)
120: current limit circuit
111: pump cell unit
111a: fitting projections (pump-cell-side fitting portions)
112: sensor cell unit
112a: fitting depression (sensor-cell-side fitting portions)
151: main electrode layer
152: surface electrode layer

DETAILED DESCRIPTION OF THE INVENTION

Figure 1B:
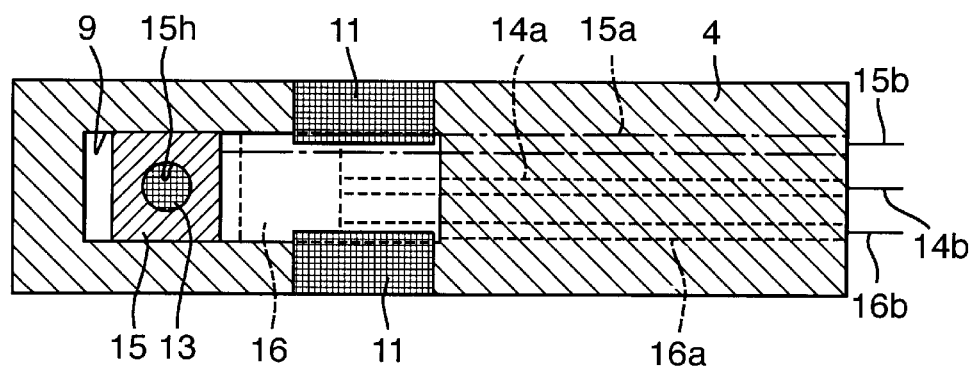
Figure 1C:
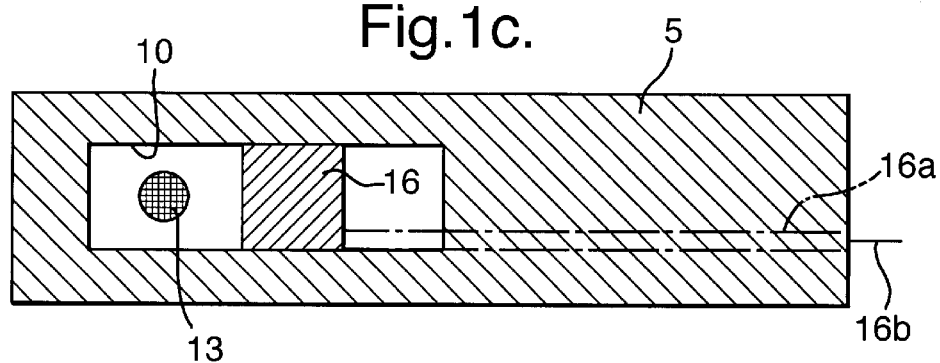

FIG. 1 shows a gas sensor 1 according to an embodiment of the present invention. The gas sensor 1 includes a first heater 2, an oxygen concentration adjustment pump element 3, an oxygen concentration cell element (oxygen concentration detection element) 4, a combustible gas component concentration detection element 5, a measurement-purpose-oxygen supply pump element 6, and a second heater 8. These elements of the gas sensor 1 are in the shape of an elongated sheet and arranged in layers in this order to thereby be integrated into a single unit. A first processing space 9 is formed between the oxygen concentration adjustment pump element 3 and the oxygen concentration cell element 4. A second processing space 10 is formed between the combustible gas component concentration detection element 5 and the measurement-purpose-oxygen supply pump element 6. Further, a spacer section 25 is integrally formed between the oxygen concentration adjustment pump element 3 and the oxygen concentration cell element 4, and the first processing space is formed by means of a space 25a of the spacer section 25.

The elements 3 to 6 and the spacer section 25 are formed of a solid electrolyte having oxygen-ion conductivity. A typical example of such a solid electrolyte is $ZrO_2$ solid solution containing $Y_2O_3$ or CaO. Another example is a solid solution of $ZrO_2$ and an oxide of an alkaline earth metal or of a rare earth metal. $ZrO_2$ serving as a base material may include $HfO_2$. The present embodiment employs a solid electrolyte ceramic of $ZrO_2$ containing $Y_2O_3$ or CaO. The first and second heaters 2 and 8, respectively, are known ceramic heaters and are adapted to heat the elements 3 to 6 to a predetermined working temperature (650° C. to 800° C.). An insulating layer (not shown in FIG. 1; an insulating layer 260 in FIG. 3) is interposed between the elements 3 to 5 and the measurement-purpose-oxygen supply pump element 6. The insulating layer is primarily formed of $Al_2O_3$. The laminated sensor structure is formed through lamination and subsequent firing of ceramic green sheets (ceramic moldings), which are to become the elements 3 to 6.

First gas passages 11 are formed at both side wall portions of the first processing space 9 so as to establish communication between the first processing space 9 and an external atmosphere to be measured. Being located on both widthwise sides of the first processing space 9 as shown in FIG. 1(b), the first gas passages 11 are interposed between and extend along the oxygen concentration adjustment pump element 3 and the oxygen concentration cell element 4 in a longitudinal direction of the elements 3 and 4. The first gas passage 11 is formed of a porous ceramic body having communicating pores, which ceramic body is a porous fired body of $Al_2O_3$ or the like. Thus, the first gas passages 11 serve as diffusion-controlling passages for introducing a measurement gas into the first processing space 9 from outside while a constant diffusion resistance is maintained.

The oxygen concentration cell element 4 and the combustible gas component concentration detection element 5 are arranged in adjacent layers. A partition wall 12, formed of an oxygen-ion-conductive solid electrolyte, is interposed between the first processing space 9 and the second processing space 10. In other words, the first and second processing spaces 9 and 10, respectively, are arranged with the partition wall 12 interposed therebetween. A second gas passage 13 is formed in the partition wall 12 so as to establish communication between the first processing space 9 and the second processing space 10. An oxygen reference electrode 14 is embedded in the partition wall 12 at a thicknesswise intermediate portion. As in the case of the first gas passages 11, the second gas passage 13 is formed of a porous ceramic body and serves as a diffusion-controlling passage for introducing a gas into the second processing space 10 from the first processing space 9 while a constant diffusion resistance is maintained. The first and second gas passages 11 and 13, respectively, may assume the form of small holes or slits instead of being formed of a porous ceramic body (or a porous metallic body).

An electrode 15 is formed on the partition wall 12 in such a manner as to be exposed to the first processing space 9. A main portion of the oxygen concentration cell element 4 is constituted by the first electrode 15, the oxygen reference electrode 14, and a portion 12a of the partition wall 12 interposed between the electrodes 15 and 14. A second electrode 16 is formed on the partition wall 12 in such a manner as to be exposed to the second processing space 10. A main portion of the combustible gas component concentration detection element 5 is constituted by the second electrode 16, the oxygen reference electrode 14, and a portion 12b of the partition wall 12 interposed between the electrodes 16 and 14. The electrodes 15 and 14 are formed at different positions in the longitudinal direction of the oxygen concentration cell element 4.

Also, the oxygen concentration adjustment pump element 3 has electrodes 19 and 20 formed on both surfaces thereof (hereinafter, the electrode 19 will be referred to as the "fourth electrode 19"). Similar to the oxygen concentration adjustment pump element 3, the measurement-purpose-oxygen supply pump element 6 has an electrode 17 formed on the surface facing the second processing space 10 and an electrode 18 formed on the opposite surface (hereinafter, the electrode 17 will be referred to as the "third electrode 17").

The electrodes 14 to 20 have a reversible catalytic function (catalytic function for oxygen dissociation), which catalyzes a dissociation reaction for dissociating oxygen molecules in order to introduce oxygen ions into solid electrolytes of the elements 3 to 6 and a recombination reaction for recombining oxygen ions in order to make the solid electrolytes release oxygen. Materials for the electrode 19 of the oxygen concentration adjustment pump element 3 and the first electrode 15 of the oxygen concentration cell element 4, which electrodes 19 and 15 are exposed to the first processing space 9, and that for the second electrode 16 of the combustible gas component concentration detection element 5, which electrode 16 is exposed to the second processing space 10, are selected such that the electrodes 19 and 15 have lower catalytic activity with respect to oxidation (i.e., combustion) of a component to be measured, such as methane, than does the electrode 16. These porous electrodes are formed in the following manner. In order to improve adhesion between an electrode and a substrate formed of a solid electrolyte ceramic, a metal or alloy powder serving as an electrode material is mixed with an appropriate amount of solid electrolyte ceramic powder similar to that used as material for the substrate. The resulting mixture is formed into a paste. Through use of the paste, an electrode pattern is printed on a ceramic green sheet serving as a substrate, followed by firing.

Figure 2:
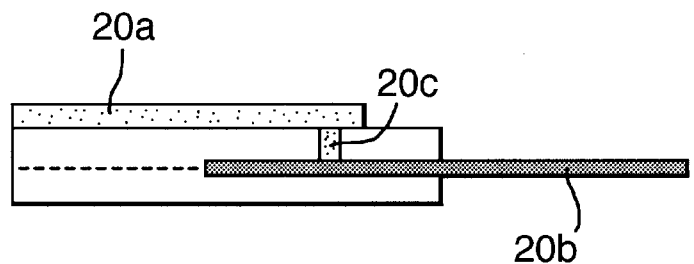
FIG. 2 is a sectional view showing an example of connection between an electrode lead and a terminal.

As shown in FIG. 1, electrode leads 14a to 20a are integrally formed with the electrodes 14 to 20, respectively, of the elements 3 to 6, and extend along a longitudinal direction of the elements 3 to 6 toward a sensor end portion. At the sensor end portion, ends of connection terminals 14b to 20b are embedded in the elements 3 to 6. As illustrated in FIG. 2, each connection terminal (20b) is electrically connected to an end portion of each electrode lead (20a) by a conductor (20c). The conductor (20c) is formed in a direction of element thickness through sintering a metallic paste.

As shown in FIG. 1, the oxygen reference electrode 14 and the second electrode 16 of the combustible gas component concentration detection element 5 are positioned in such a manner as not to interfere with the second gas passage 13. This feature further stabilizes an sensor output indicative of a combustible gas component concentration. The first electrode 15 of the oxygen concentration cell element 4 overlaps the second gas passage 13. In order to permit gas flow, a through-hole 15h is formed in the first electrode 15 at a position corresponding to the second gas passage 13.

Figure 3A:
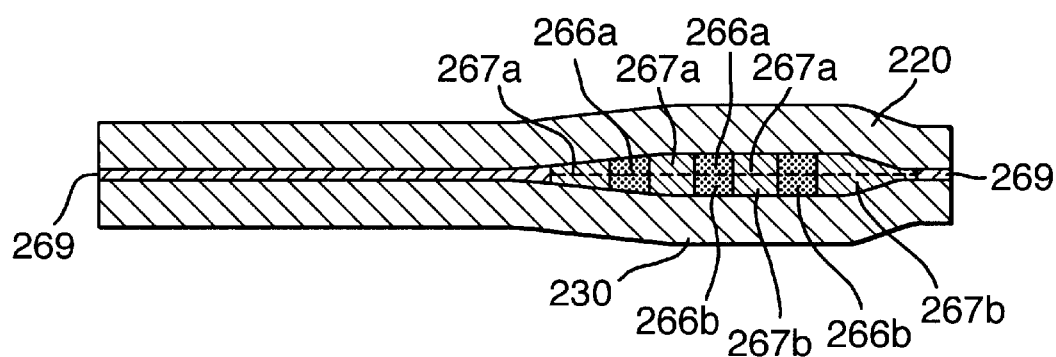
FIG. 3 shows explanatory views illustrating a process of forming a processing space in the gas sensor of FIG. 1.
Figure 3B:
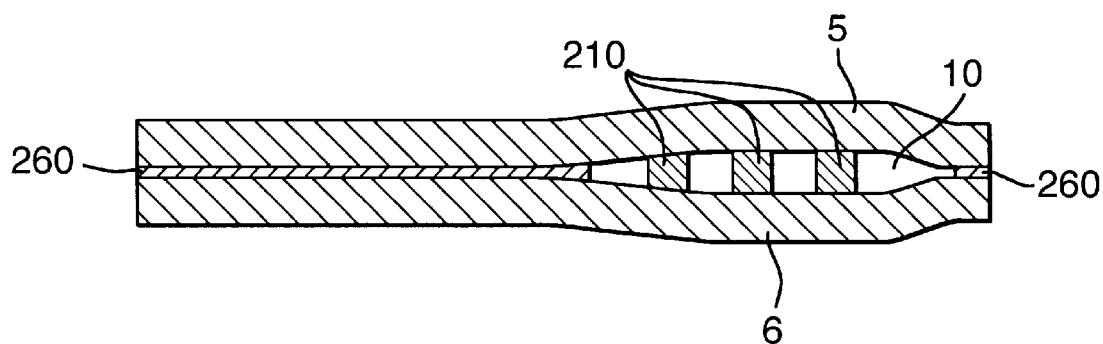

As shown in FIG. 3(b), in at lest one of the first processing space 9 and the second processing space 10 (in the second processing space 10 in the present embodiment), supports 210 are formed in a scattered or staggered manner to thereby prevent the collapse of the spaces 9 and 10 during firing. As shown in FIG. 3(a), through use of ceramic powder paste (for example, paste of porous $Al_2O_3$ powder), support patterns 266a are formed on a ceramic green sheet 220 in a region for defining the second processing space 10. The ceramic green sheet 220 will be formed into the combustible gas component concentration detection element 5. Likewise, support patterns 266b are formed on a ceramic green sheet 230 in a region for defining the second processing space 10. The ceramic green sheet 230 will be formed into the measurement-purpose-oxygen supply pump element 6. The support patterns 266a and 266b will be formed into supports 210. Through use of a paste material (for example, carbon paste) which will be burned or decomposed during firing, auxiliary support patterns 267a are formed on the ceramic green sheet 220 in a region for defining the first processing space 9 in such a manner as not to overlap the support patterns 266a. Likewise, auxiliary support patterns 267b are formed on the ceramic green sheet 230 in a region for defining the first processing space 9 in such a manner as not to overlap the support patterns 266b. Further, through use of Al₂O₃ powder paste, an insulating layer pattern serving as a bonding coat 269 is formed between the ceramic green sheets 220 and 230 in a region other than the region for defining the first processing space 9. The thickness of the insulating layer pattern is made smaller than that of the supports 210.

The thus-prepared assembly of the ceramic green sheets 220 and 230 is subjected to firing. As a result, as shown in FIG. 3(b), the support patterns 266a and 266b are united into the supports 210 between the combustible gas component concentration detection element 5 and the measurement-purpose-oxygen supply pump element 6, whereas the auxiliary patterns 267a and 267b are disappeared. The second processing space 10 is formed, while its size is maintained by the supports 210. The combustible gas component concentration detection element 5 and the measurement-purpose-oxygen supply pump element 6 are bonded together in a region other than the second processing space 10 by means of the insulating layer 260, which is formed from the bonding coat 269.

Figure 4A:
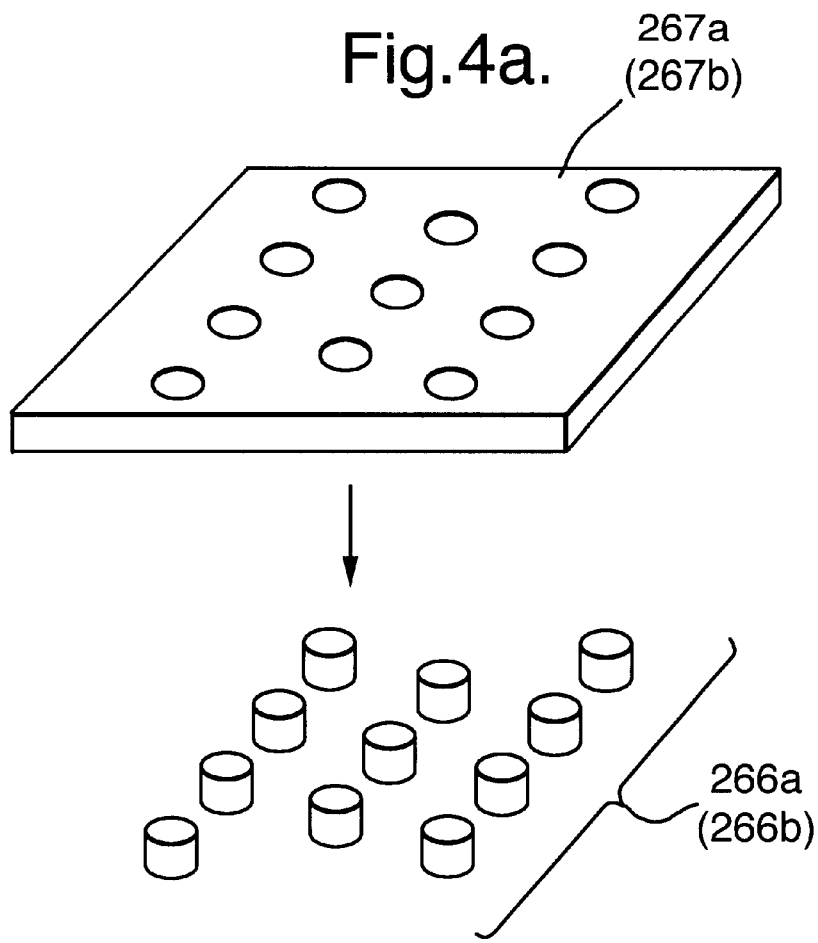
FIG. 4 shows explanatory views illustrating the process of forming the processing space in the gas sensor of FIG. 1.
Figure 4B:
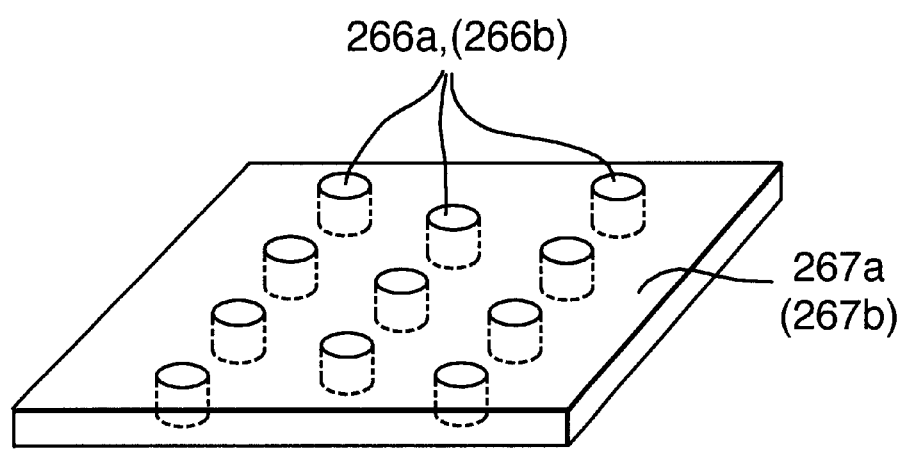

As shown in FIG. 4, the support patterns 266a (266b) and the auxiliary support pattern 267a (267b) are complementarily formed to thereby form a substantial plane. When the green sheets 220 and 230 are superposed each other as shown in FIG. 3(a), the reinforcing effect of the auxiliary support patterns 267a and 267b prevents or suppresses the collapse of the support patterns 266a and 266b butting against each other. As exaggeratedly shown in FIG. 3(a), even when the bonding coat 269 is made considerably thinner than the total thickness of the support patterns 266a and 266b, the green sheets 220 and 230 can be bonded together by means of the interposed bonding coat 269. Since the green sheets 220 and 230 are flexible, the bonding can be established through slight flexure thereof. Thus, the green sheets 220 and 230 can be smoothly fired into a single unit.

As shown in FIG. 1, the entire sensor 1 is divided into two at an interference between the spacer section 25 and the oxygen concentration cell element 4. Thus, there is formed a pump cell unit 111 including the oxygen concentration adjustment pump element 3, and a sensor cell unit 112 including the oxygen concentration cell element 4 (oxygen concentration detection element), the second processing space 10, the combustible gas component concentration detection element 5, and the measurement-purpose-oxygen supply pump element 6. The pump cell unit 111 and the sensor cell unit 112 are superposed on each other such that the fourth electrode 19 faces the first electrode 15, and are joined and integrated together through use of bonding material such as glass applied to the superposition surfaces through which they are superposed on each other. Further, at the widthwise opposite sides of the superposition surface of the pump cell unit 111 are formed rib-shaped fitting projections 111a (pump-cell-side fitting portion) that extend along the edges of the pump cell unit 111. The fitting portions 111a are fitted into the fitting depressions 112a (sensor-cell-side fitting portions) formed on the sensor cell unit 112 at corresponding portions for positioning during superposition.

Figure 6A:
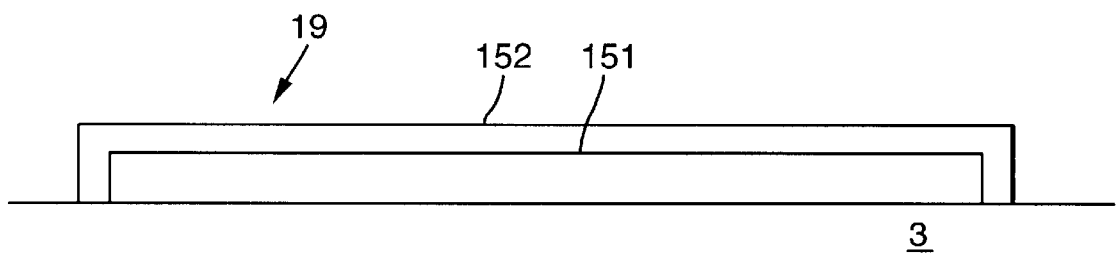
FIG. 6 is a schematic view showing the structure of the fourth electrode.

As shown in FIG. 6(a), the fourth electrode 19 has a two-layer structure composed of a porous main electrode layer 151 and a porous surface electrode layer 152 that forms a surface portion of the fourth electrode 19. The main electrode layer 151 is formed of Pt or a Pt—Au alloy (in the present embodiment, substantially the entire portion is formed of Pt). The surface electrode layer 152 is formed of an Au-containing metal that contains Au as a main component (in the present embodiment, substantially the entire portion is formed of Au). The first electrode 15 shown in FIG. 1 is formed of a porous metal such as porous Pt or a porous Pt—Au alloy (Au content: not greater than 1 wt. %) (in the present embodiment, substantially the entire portion is formed of Pt) as in the case of other electrodes except for the fourth electrode 19.

Since the surface of the porous main electrode layer 151 formed of Pt—which has a high activity of dissociating oxygen molecules—is covered with the porous surface electrode layer 152 formed of Au—which has a low catalytic activity for combustion of a combustible gas component, the catalytic activity for combustion of the combustible gas component within the first processing space can be decreased, while the activity of dissociating oxygen molecules is maintained at a sufficient level. Thus, there can be prevented loss of a combustible gas component such as HC to be detected, so that the sensor sensitivity can be increased. In the case where substantially the entire portion of the main electrode layer 151 is formed of Pt and substantially the entire portion of the surface electrode layer 152 is formed of Au, it is preferred that the value of $\{WAu/(WPt+WAu)\} \times 100$ fall within the range of 2–20 wt. %, preferably 3–10 wt. %, where WPt is the Pt content by weight of the fourth electrode 19, and WAu is the Au content by weight of the fourth electrode 19. When the value is less than 2 wt. %, the combustion catalytic activity of the fourth electrode 19 cannot be decreased sufficiently, with a possible result that the sensitivity of the sensor decreases. By contrast, when the value exceeds 20 wt. %, the catalytic activity of the fourth electrode 19 for dissociation and recombination of oxygen molecules decreases excessively, with a possible result that the function of the oxygen concentration adjustment pump element 3 becomes insufficient.

Figure 6B:
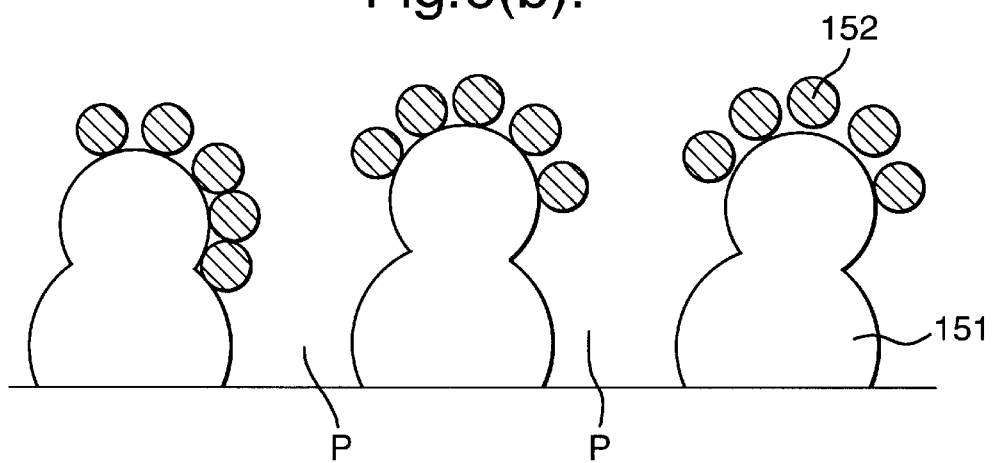
Figure 6C:
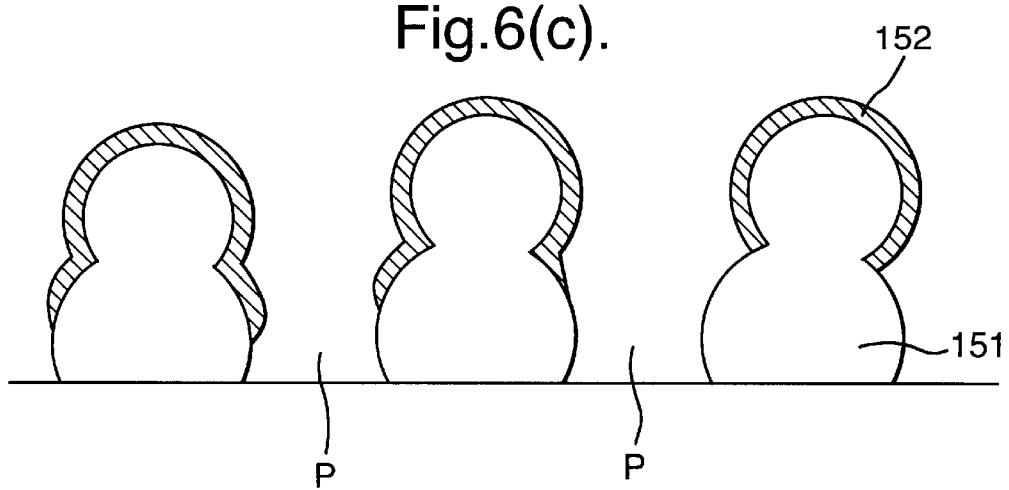

A method shown in FIG. 6(b) may be used to form the surface electrode layer 152 on the main electrode layer 151. That is, paste containing particles of a material for the surface electrode layer 152 is applied onto the fired main electrode layer 151, and is then fired at a temperature lower that for the firing of the main electrode layer 151. Alternatively, as shown in FIG. 6(c), the surface electrode layer 152 may be formed through vapor-phase film formation such as vacuum deposition or sputtering. As shown in FIGS. 6(b) and (c), since many voids P are formed in the porous main electrode layer 151 in a complex manner, the surface electrode layer 152 may be formed such that its material fails to enter deeply into the voids P. In this case, parts of the main electrode layer 151 are not covered by the surface electrode layer 152 and remain exposed. However, since such exposed portions exhibit a strong catalytic activity for dissociation and recombination of oxygen molecules, the formation of such exposed portions is rather preferable in terms of securing the function of the oxygen concentration adjustment pump element.

Figure 5:
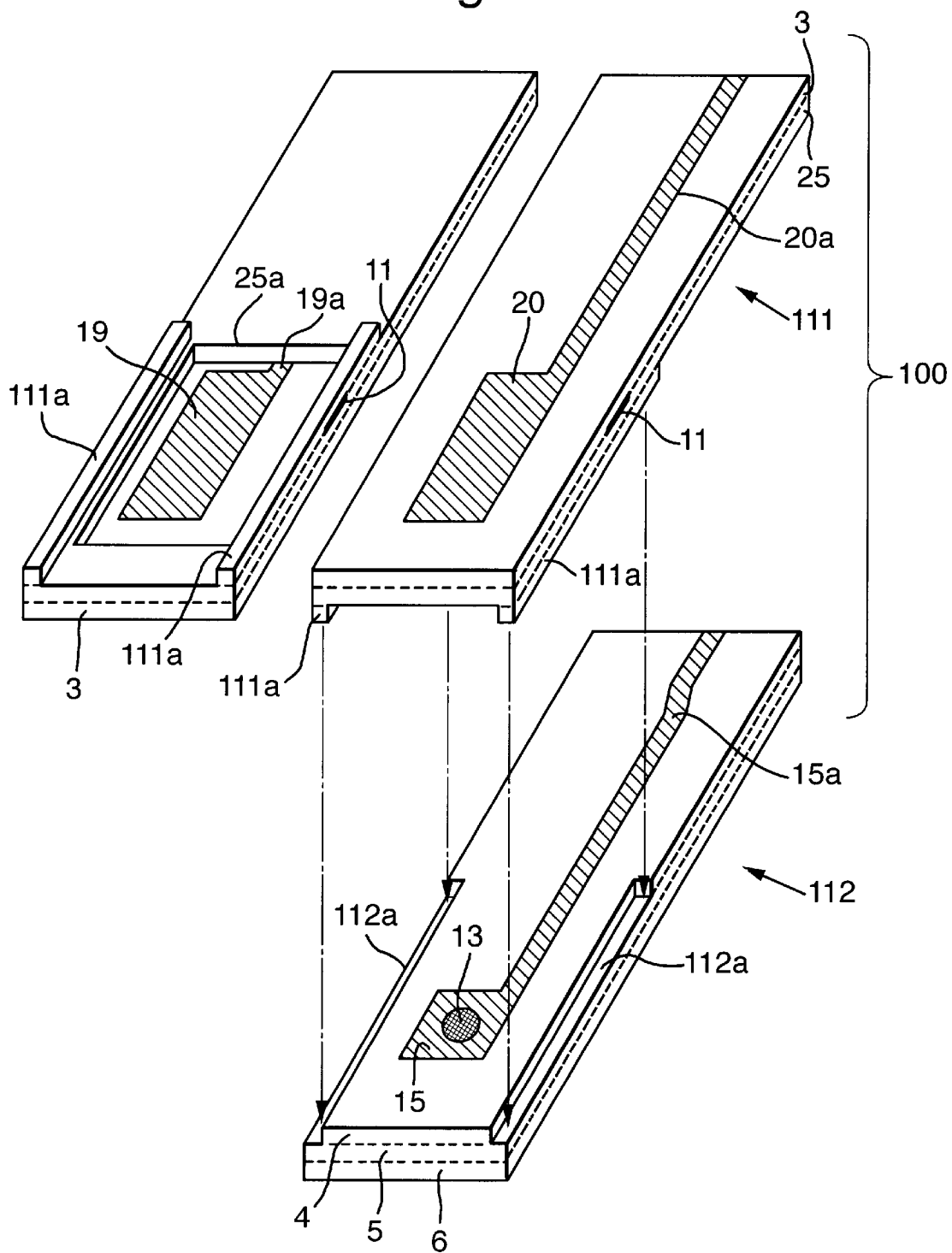
FIG. 5 is an exploded perspective view showing the gas sensor of FIG. 1 together with the reverse side of the pump cell unit.

An example process for manufacturing the pump cell unit 111 and the sensor cell unit 112 shown in FIGS. 1 and 5 will be described with reference to FIGS. 7 and 8. FIG. 7 shows a laminate structure of a first unfired assembly 211 used for manufacturing the pump cell unit 111. The first unfired assembly 211 includes a first portion 211a and a second portion 211b. The first portion 211a is mainly composed of a ZrO₂ green sheet (hereinafter may be referred to as merely a green sheet) 220, which will become the oxygen concentration adjustment pump element 3. The second portion 211b is mainly composed of a green sheet 231, which will serve as the spacer section 25. The green sheet is formed through sheeting a kneaded mixture of a ZrO₂ powder, a forming aid such as an organic binder, and an organic solvent.

In the first portion 211a, through use of $Al_2O_3$ paste or the like, insulating coats (insulating layer patterns) 221 and 222 for insulating the leads 20a and 19a from the oxygen concentration adjustment pump element 3 are formed on the corresponding surfaces of the green sheet 220 in regions other than those corresponding to the electrodes 20 and 19 (FIG. 1). After the insulating coats 221 and 222 are formed, electrode patterns 223 and 224a for forming the electrodes 20 and 19 (only a main electrode layer 151 for the electrode 19 (FIG. 5)) and the leads 20a and 19a are formed through printing and through use of Pt paste or the like. A protective over coat 225 is formed on the electrode pattern 223, which will serve as the outer electrode 20, through use of $Al_2O_3$ paste or the like.

In the second portion 211b, insulating coats 230 and 232 are formed on the corresponding surfaces of the green sheet 231 in a manner similar to that for the first portion 211a. A pattern 229, which will serve as a first gas passage 11, is formed on the insulating coat 230 through use of $Al_2O_3$ paste. Green sheets 234, which will serve as fitting projections 111a, are bonded onto the insulating coat 232 through use of bonding coats 233 (formed from alumina paste).

The first portion 211a and the second portion 211b are bonded together through use of a bonding coat 228, while end portions of Pt—Rh alloy wires 227a and 227b, which will serve as terminals of the electrodes 20 and 19, are sandwiched between the portions 211a and 211b. The thus-obtained first unfired assembly 211 is fired to obtain a pump cell unit in which a surface electrode layer 152 (FIG. 6) of the fourth electrode 19 is not yet formed. Then, as shown in FIG. 7, through use of Au paste, a pattern 224b is printed on the fired main electrode layer at the corresponding position, followed by secondary metallization. In the secondary metallization, the printed pattern 224b is fired at a temperature (for example, 850° C. to 1000° C.) lower than a ceramics firing temperature. Thus, the multilayered fourth electrode 19 is formed, thereby completing the pump cell unit 111.

Figure 8:
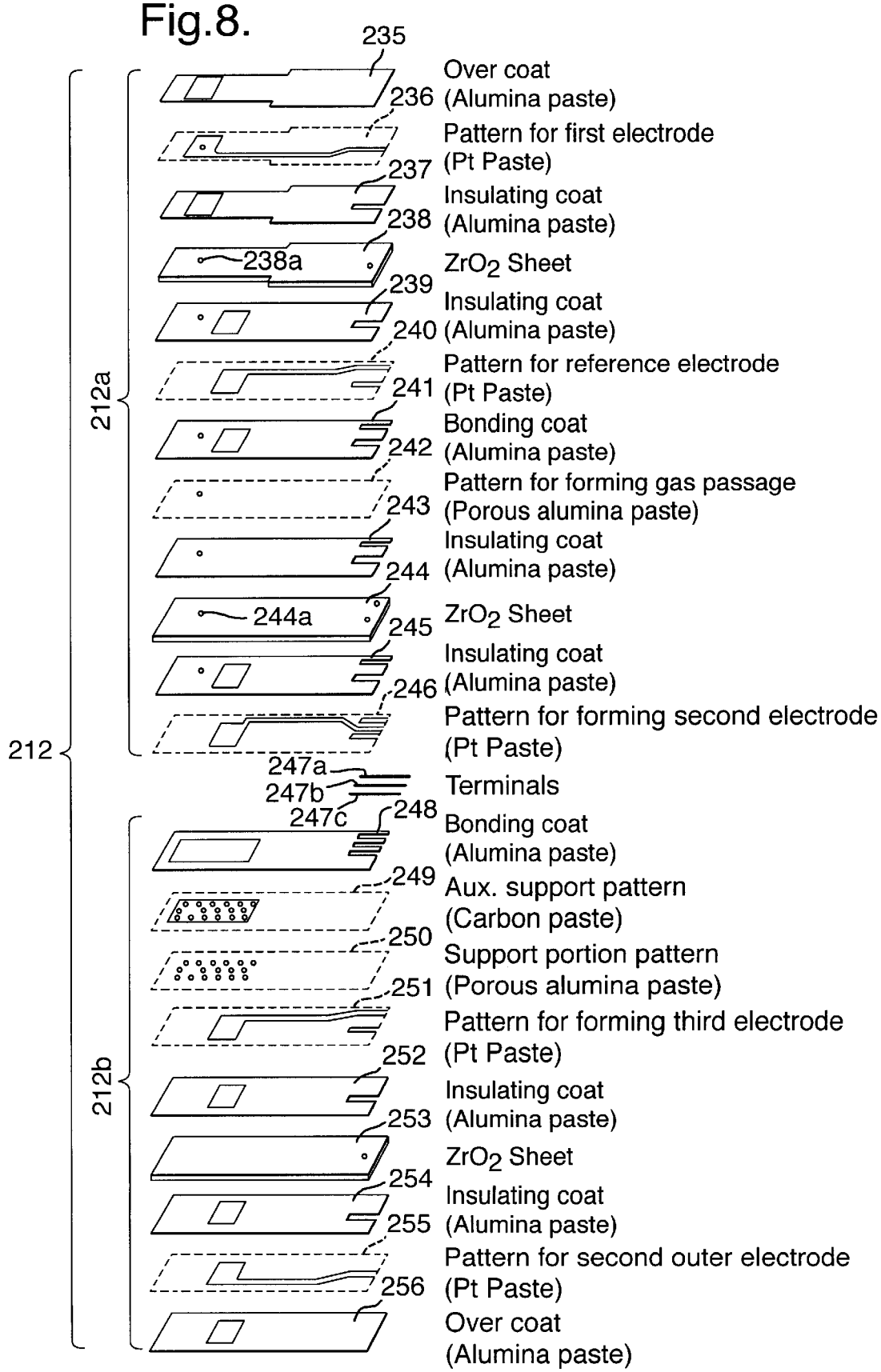
FIG. 8 gives perspective views showing a method of manufacturing the sensor cell unit of the gas sensor of FIG. 1.

FIG. 8 shows a laminate structure of a second unfired assembly 212 used for manufacturing the sensor cell unit 112. The second unfired assembly 212 includes a first portion 212a and a second portion 212b. The first portion 212a is mainly composed of a green sheet 238, which will serve as a main portion of the oxygen concentration cell element 4, and a green sheet 244, which will serve as a main portion of the combustible gas component concentration detection element 5. The second portion 212b is mainly composed of a green sheet 253, which will serve as the measurement-purpose-oxygen supply pump element 6.

In the first portion 212a, insulating coats (insulating layer patterns) 237 and 239 for insulating the leads 15a and 14a from the oxygen concentration cell element 4 are formed on the corresponding surfaces of the green sheet 238 in regions other than those corresponding to the electrodes 15 and 14 (FIG. 1). After the insulating coats 237 and 239 are formed, electrode patterns 236 and 240 for forming the electrodes 15 and 14 and the leads 15a and 14a are formed through printing and through use of Pt paste or the like. Insulating coats 243 and 245 are formed on the corresponding surfaces of the green sheet 244. An electrode pattern 246 for forming the electrode 16 and the lead 16a is formed on the insulating coat 245. The thus-processed green sheets 238 and 244 are bonded together through use of a bonding coat 241. Through-holes 238a and 244a for forming the second gas passage 13 are formed in the green sheets 238 and 244. Printing of a pattern 242 causes the through-holes 238a and 244a to be filled with $Al_2O_3$ paste. Cuts, which will serve as fitting depressions 112a (FIG. 5), are formed in the green sheet 238 at widthwise edge portions.

In the second portion 212b, insulating coats 252 and 254 are formed on the corresponding surfaces of the green sheet 253. A pattern 251 for forming the third electrode 17 (FIG. 1) is formed on the insulating coat 252 through printing and through use of Pt paste or the like. A support portion pattern 250 and an auxiliary support pattern 249 are formed above the insulating coat 252 in order to form the second processing space 10 in a manner similar to that shown in FIG. 4. Similarly, a pattern 255 for forming the electrode 18 is formed on the insulating coat 254 through printing and through use of Pt paste or the like. Moreover, an over coat 256 is formed on the electrode pattern 225 through use of alumina paste.

The first portion 212a and the second portion 212b are bonded together through use of a bonding coat 248, while end portions of Pt—Rh alloy wires 247a, 247b, and 247c, which will serve as terminals of the electrodes 14 to 20 are sandwiched between the portions 212a and 212b. The thus-obtained second unfired assembly 212 is fired to obtain the sensor cell unit 112 shown in FIG. 5.

Next will be described an exemplary configuration of a gas sensor system using the gas sensor 1 described above.

Figure 9:
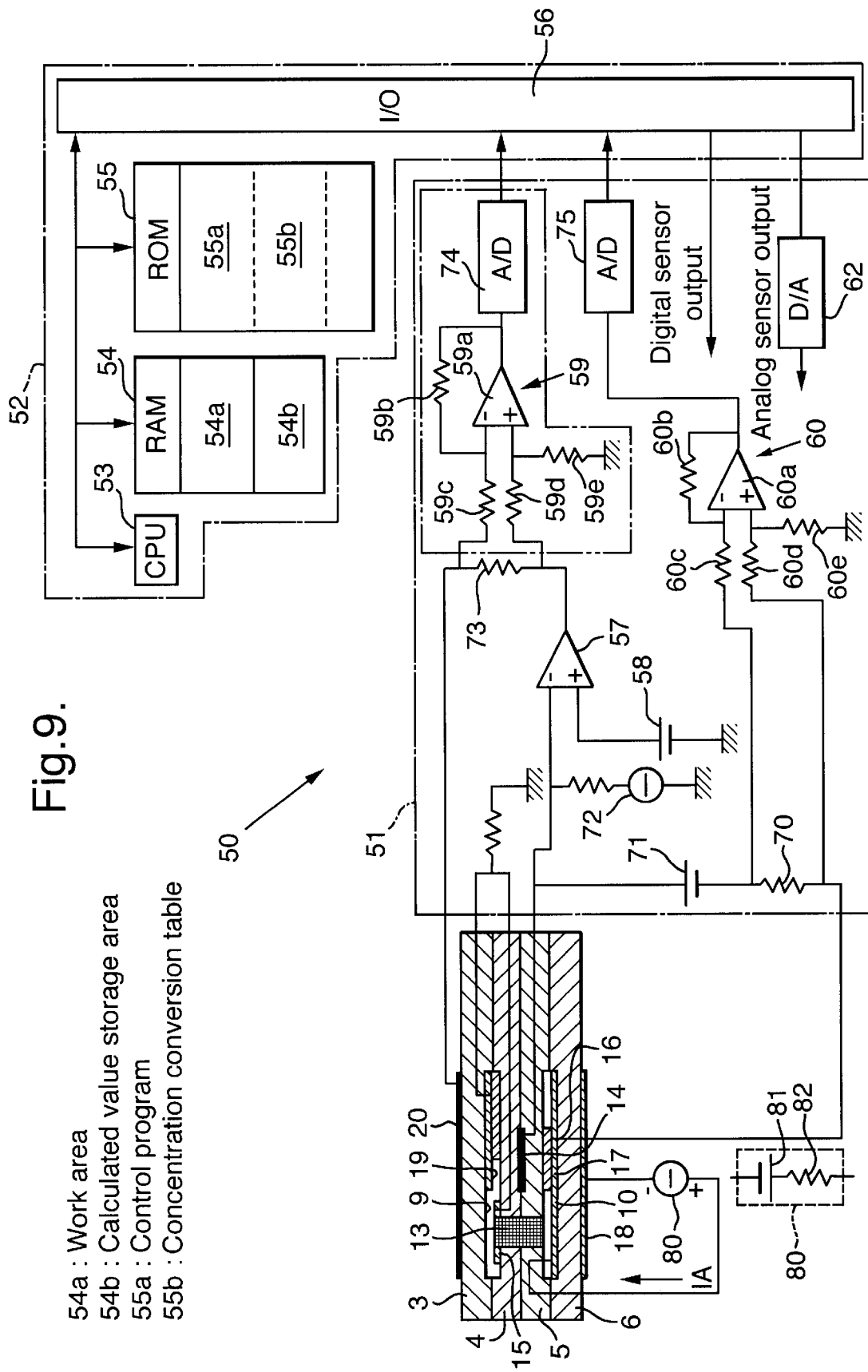
FIG. 9 is a block diagram showing a circuit configuration example of a gas sensor system using the gas sensor of FIG. 1.

FIG. 9 is a block diagram showing an exemplary electrical configuration of a gas sensor system (hereinafter simply referred to as the "sensor system") using the gas sensor 1. Specifically, a gas sensor system 50 includes the gas sensor 1, a microprocessor 52, and a peripheral circuit 51 for connecting the gas sensor 1 to the microprocessor 52. The microprocessor 52 is a main portion of an output conversion unit and includes an I/O port 56 serving as an input/output interface, a CPU 53, a RAM 54, a ROM 55, etc. The CPU 53, the RAM 54, the ROM 55, and the like are connected to the I/O port 56. The RAM 54 has a work area 54a for the CPU 53, and a storage area 54b for storing calculated values of component concentration. The ROM 55 contains a control program 55a and an HC concentration conversion table 55b. The control program 55a is used for controlling the gas sensor system 50 in computing a component concentration to be output and in outputting the computed component concentration. The CPU 53 serves as concentration determination means and determines a component concentration according to the control program 55a stored in the ROM 55.

In the gas sensor system 50, the gas sensor 1 operates in the following manner. The gas sensor 1 is heated to a predetermined working temperature by the first heater 2 and the second heater 8 shown in FIG. 1 (either of the heaters may be omitted). The working temperature is a temperature at which $ZrO_2$ solid electrolyte, of which the elements 3 to 6 are formed, is activated. While the gas sensor 1 is heated at its working temperature, exhaust gas, which is a measurement gas, is introduced into the first processing space 9 through the gas passages 11. The oxygen concentration cell element 4 measures the oxygen concentration of the introduced exhaust gas. Based on the oxygen concentration detected by the oxygen concentration cell element 4, the oxygen concentration adjustment pump element 3 pumps out oxygen from or pumps oxygen into the gas contained in the first processing space 9 so as to bring the oxygen concentration to a predetermined target value of $10^{-12}$ atm to $10^{-6}$ atm (preferably $10^{-11}$ atm to $10^{-9}$ atm), in other words, to a predetermined target value at which a reaction of decomposing water vapor contained in the exhaust gas is not substantially initiated. Generally, the oxygen concentration of the exhaust gas is higher than the above target value. In this case, the oxygen concentration adjustment pump element 3 operates so as to reduce the oxygen concentration of the first processing space 9.

After being reduced in its oxygen concentration to a predetermined value, the gas contained in the first processing space 9 flows into the second processing space 10 through the second gas passage 13. Since the second electrode 16 is set higher than the first electrode 15 in catalytic activity for oxidation of a combustible gas component such as HC or the like, a combustible gas component of the gas contained in the second processing space 10 is burned while the second electrode 16 serves as an oxidation catalyst section. Thus, oxygen is consumed. The oxygen concentration of the second processing space 10 varies according to oxygen consumption associated with the combustion, i.e., according to the concentration of a combustible gas component.

By use of a constant current power source 80, constant current is caused to flow between the electrodes 17 and 18 of the measurement-purpose-oxygen supply pump element 6 such that the third electrode 17 becomes positive. As a result, a constant amount of oxygen used for measurement of the combustible gas component in the measurement gas is pumped into the second processing space 10. In the present embodiment, the constant current power source 80 is composed of a constant voltage power source 81 and a resistor 82 which is connected to the constant voltage power source 81 and which has a resistance sufficiently greater than (e.g., 500 to 5000 times) the internal resistance of the oxygen concentration detection element 4 as measured at a sensor operation temperature. However, the constant current power source 80 may employ a different configuration. The current supplied by the constant current power source 80 is properly set such that oxygen is supplied to the second processing space 10 in a slightly excessive amount in order to guarantee that the current always flows through the combustible gas component concentration detection element 5 in a direction for pumping out oxygen.

A constant DC-voltage power source 71 (FIG. 9) applies a constant voltage VC to the combustible gas component concentration detection element 5 via the electrodes 14 and 16. In the present embodiment, the polarity of the applied voltage VC is set such that the second electrode 16 becomes negative, or oxygen is pumped out from the second processing space 10. The voltage VC is set within the range in which the current flowing through the element 5 becomes substantially zero when the combustible gas component content of the gas is substantially zero, and the partial pressure of oxygen in the second processing space 10 does not drop to a value at which decomposition of nitrogen oxides (NOx) contained in the exhaust gas is initiated.

An output current of the combustible gas component concentration detection element 5 varies according to oxygen consumption associated with combustion of a combustible gas component contained in the gas introduced into the second processing space 10. Accordingly, the combustible gas component concentration of the exhaust gas can be determined from the output current. As the amount of oxygen consumed in the second processing space 10 due to combustion therein increases, the concentration cell electromotive fore—which is produced by the combustible gas component concentration detection element 5 and which has a polarity opposite the voltage VC—increases. Therefore, when the direction of application of the voltage VC is defined as positive, the output current of the element 5 decreases as the combustible gas component concentration increases.

The circuit configuration and operation of the sensor system 50 will be described in more detail with reference to FIG. 9. In the gas sensor 1, there are grounded the first electrode 15 of the oxygen concentration cell element 4 and the electrode 19 of the oxygen concentration adjustment pump element 3 exposed to the first processing space 9. The oxygen reference electrode 14 is connected to an input terminal of a differential amplifier 57. The constant DC-voltage power source 71 is connected to the combustible gas component concentration detection element 5 so as to apply the voltage VC to the element 5 via the electrodes 14 and 16 as described previously. Thus, an electromotive force E of the oxygen concentration cell element 4 and the voltage VC are input in a superimposed manner to the above-mentioned input terminal of the differential amplifier 57.

A power supply circuit 58 is connected to the other input terminal of the differential amplifier 57. The power supply circuit 58 supplies to the differential amplifier 57 a target electromotive force EC corresponding to a target oxygen concentration value (in actuality, a set voltage is (EC+VC)). The differential amplifier 57 amplifies the difference between the electromotive force E of the oxygen concentration cell element 4 and the target electromotive force EC, and inputs the amplified difference to the electrode 20 of the oxygen concentration adjustment pump element 3. Upon reception of the output from the differential amplifier 57, the oxygen concentration adjustment pump element 3 causes oxygen to be pumped out from or pumped into the first processing space 9 so that the electromotive force E (corresponding to the oxygen concentration of the first processing space 9) approaches the target electromotive force EC. That is, the differential amplifier 57 serves as the oxygen pump operation control means. The power supply circuit 58 may be configured such that the target electromotive force EC is fixedly set through output of a fixed voltage or such that the target electromotive force EC is variably set.

The oxygen concentration cell element 4 and the combustible gas component concentration detection element 5 share the common oxygen reference electrode 14. However, a constant current power source 72 causes a small DC current to continuously flow between the oxygen reference electrode 14 and the first electrode 15 (or the second electrode 16) in such a direction that oxygen is pumped into the oxygen reference electrode 14 (that is, the oxygen reference electrode 14 serves as a self-generation-type reference electrode). This feature causes pores formed in the oxygen reference electrode 14 to be always filled with a reference gas of near 100% oxygen. Thus, an electromotive force of the oxygen concentration cell element 4 and of the combustible gas component concentration detection element 5 is increased, thereby improving the measuring accuracy and the measuring sensitivity of the gas sensor 1.

A voltage applied by the constant current power source 72 is set such that the voltage becomes sufficiently smaller than the electromotive force E output from the oxygen concentration cell element 4 and such that the oxygen concentration of the oxygen reference electrode 14 becomes near 100%.

An output current of the combustible gas component concentration detection element 5 is detected, for example, in the form of the difference between voltages as measured at both ends of a resistor 70 for current measurement use. In the present embodiment, the output current signal undergoes voltage conversion effected by a differential amplifier 60 (including an operational amplifier 60a and peripheral resistors 60b to 60e), followed by analog-to-digital conversion effected by an A/D converter 75. The thus-obtained digital signal is input to the microprocessor 52.

Figures 10, 11:
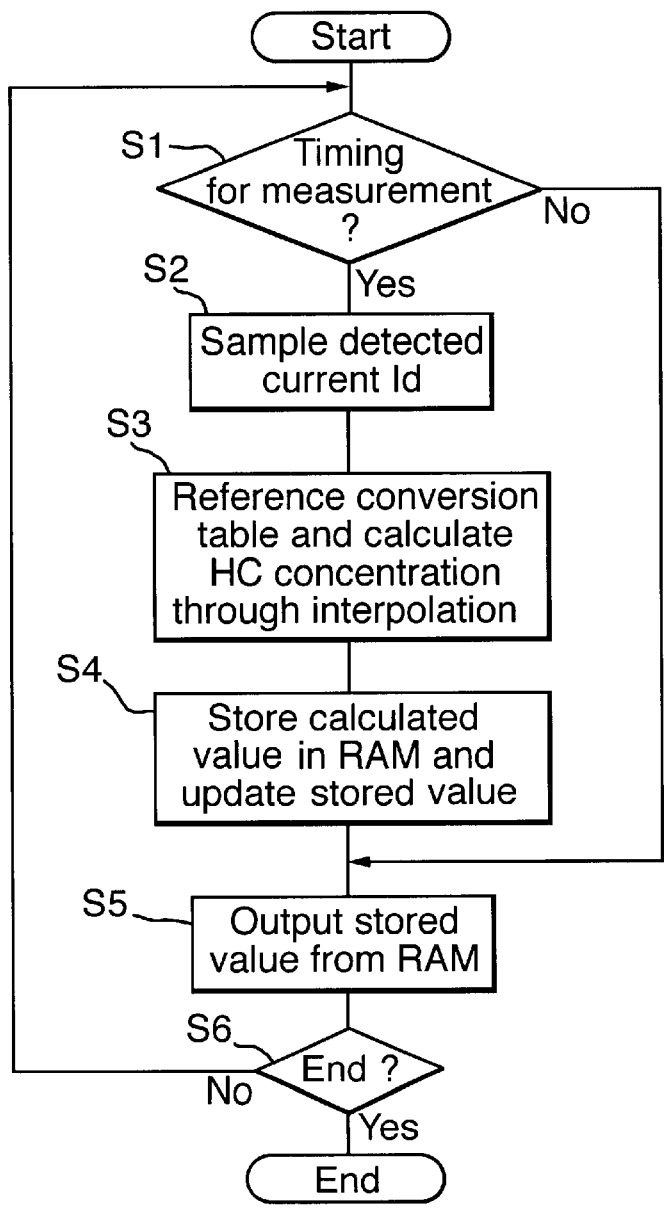
FIG. 10 gives an explanatory diagram showing a contents example of a concentration conversion table.
FIG. 11 is a flowchart showing a process flow of a control program of the gas sensor system of FIG. 9.

The ROM 55 of the microprocessor 52 contains the control program 55a and the concentration conversion table 55b as mentioned previously. FIG. 10 shows an example the contents of the concentration conversion table 55b. The table 55b contains values of detection current Id1, Id2, Id3, etc. of the combustible gas component concentration detection element 5 corresponding to values of combustible gas component concentration (for example, values of HC concentration) C1, C2, C3, etc. These values are previously determined based on experiments and the like. The CPU 53 (FIG. 9) performs sensor output control as represented by the flowchart of FIG. 11 according to the control program 55a, using the RAM 54 as a work area.

Specifically, timing for measurement is metered by an unillustrated timer. In step S1, when timing for measurement is reached, processing proceeds to step S2. In step S2, the CPU 53 samples the detection current Id output from the combustible gas component concentration detection element 5. In step S3, the CPU 53 calculates a combustible gas component concentration corresponding to the sampled value through interpolation while referencing the concentration conversion table 55b of FIG. 10. In step S4, the CPU 53 stores the calculated value into the calculated value storage area 54b of the RAM 54. The newly stored value overwrites a corresponding value stored previously in the area 54b. In step S5, the CPU 53 outputs the newly written calculated value from the I/O port 56 as information regarding the combustible gas component concentration of an exhaust gas. The output may be either digital or analog. An analog output is obtained through digital-to-analog conversion effected by a D/A converter 62 connected to the I/O port 56.

In the thus-configured and -operating gas sensor system 50, the oxygen concentration of the exhaust gas introduced into the first processing space 9 is adjusted to a predetermined value of $10^{-12}$ atm to $10^{-6}$ atm through operation of the oxygen concentration adjustment pump element 3. The thus-treated gas is introduced into the second processing space 10 and burned. The detection current Id of the combustible gas component concentration detection element 5 varies according to oxygen consumption associated with the combustion. Thus, an output representing the detection current is utilized as information regarding the combustible gas component concentration of the exhaust gas. Through operation of the oxygen concentration adjustment pump element 3, the oxygen concentration of the first processing space 9 is adjusted to a value at which a reaction of decomposing water vapor contained in the exhaust gas is not substantially initiated. Even when the decomposition reaction is initiated, the degree of the reaction is very small. Thus, there is very effectively prevented an impairment in accuracy in measuring a combustible gas component concentration which would otherwise result from combustion of hydrogen generated from decomposition of water vapor.

Figure 12:
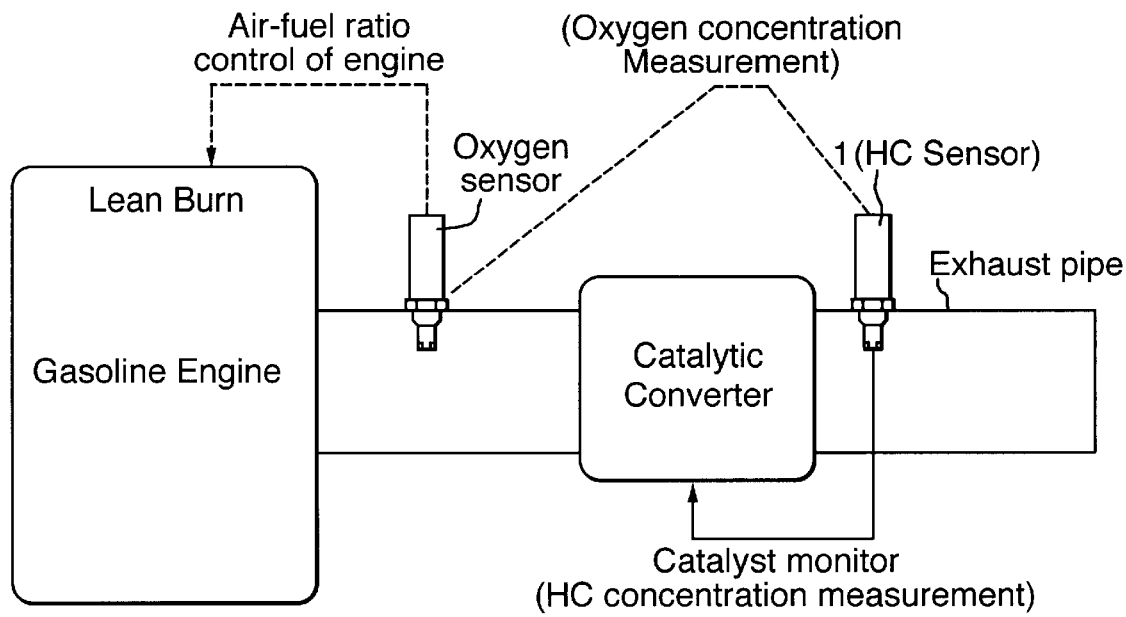
FIG. 12 is a schematic diagram showing an example in which the gas sensor of the present invention is used as an HC detection sensor for a gasoline engine.

Next will be described applications of the gas sensor 1 or the gas sensor system 50. FIG. 12 schematically shows an exhaust gas purification system of a gasoline engine. An oxygen sensor, a three way catalytic converter, and the gas sensor 1 of the present invention are attached onto an exhaust pipe in this order starting from the engine side. The oxygen sensor is used for air-fuel ratio control. The three way catalytic converter concurrently performs oxidation of HC and reduction of NOx to thereby purify an exhaust gas. The gas sensor 1 has a function to serve as an oxygen sensor for measuring the oxygen concentration of the purified exhaust gas, which will be described later. The gas sensor 1 measures the HC concentration of the purified exhaust gas, for example, in order to judge whether the catalyst is deteriorated.

Figure 13:
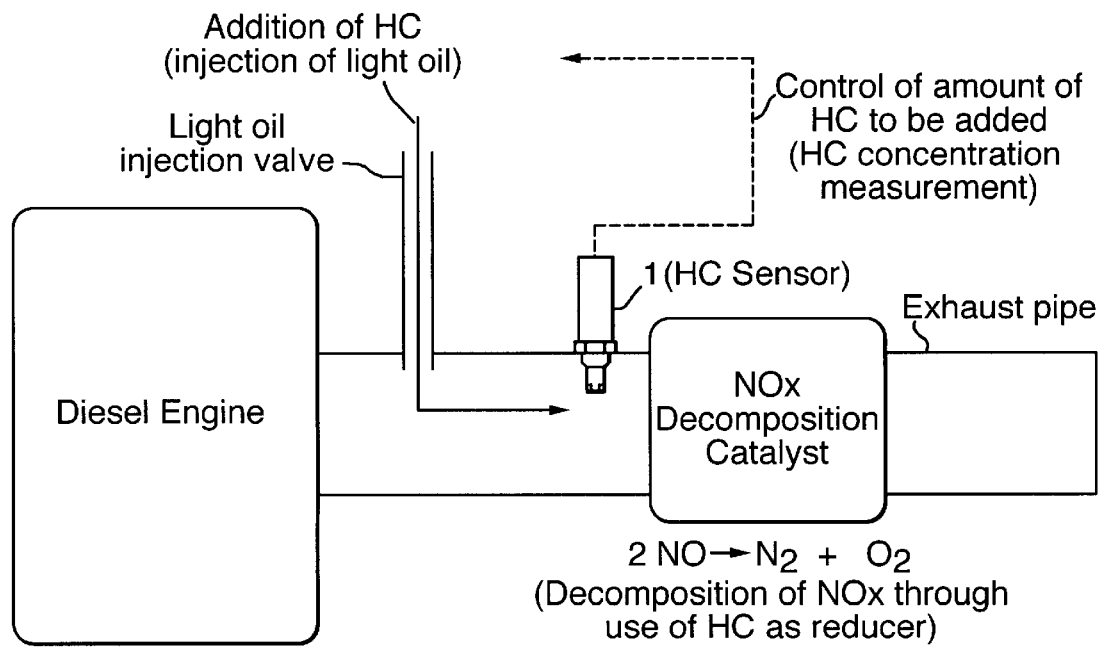
FIG. 13 is a schematic diagram showing an example in which the gas sensor of the present invention is used as an HC detection sensor for a diesel engine.

FIG. 13 schematically shows an exhaust gas purification system of a diesel engine. A light oil injection valve and an NOx decomposition catalyst are attached onto an exhaust pipe in this order starting from the engine side. The light oil injection valve is used for injecting light oil serving as an HC source into an exhaust gas. The NOx decomposition catalyst decomposes NOx into nitrogen and oxygen while using HC added through light oil injection as a reducer, thereby purifying the exhaust gas. The gas sensor 1 of the present invention is disposed on the upstream side of the NOx decomposition catalyst and monitors the HC concentration of the light-oil-injected exhaust gas in order to feedback-control the amount of light oil to be injected into the exhaust gas.

In the gas sensor 1, the oxygen concentration cell element 4 and the combustible gas component concentration detection element 5 are each formed of a $ZrO_2$ solid catalyst. In the case of an oxygen concentration cell element formed of a $ZrO_2$ solid electrolyte and configured such that one electrode is in contact with a gas to be measured, which gas contains oxygen and a combustible gas component, whereas the other electrode is in contact with a reference atmosphere having a constant oxygen concentration, its electromotive force varies abruptly when a gas composition falls outside a stoichiometric composition in which oxygen and a combustible gas component are present in a proper ratio so that they react with each other completely. When an ordinary gasoline engine or diesel engine is operated under lean-burn conditions, an exhaust gas emitted from the engine contains combustible gas components in a total concentration of about 0 to 1000 ppmC. An exhaust gas having such a combustible gas component concentration is introduced into the first processing space 9, and the oxygen concentration of the introduced exhaust gas is adjusted to $10^{-6}$ atm (preferably $10^{-9}$ atm) or lower as mentioned previously. As a result, a gas introduced into the second processing space 10 from the first processing space 9 has a stoichiometric composition or a composition shifted slightly toward a rich condition. Thus, an output electromotive force of the combustible gas component concentration detection element 5 is increased, thereby improving the sensitivity of the gas sensor 1.

In the gas sensor system 50, after the oxygen concentration of the first processing space 9 is reduced to a predetermined value, the combustible gas component concentration of the second processing space 10 is measured. Accordingly, a detected output of the combustible gas component concentration detection element 5 is substantially less affected by the oxygen concentration of an exhaust gas. However, when a detected output of the combustible gas component concentration detection element 5 somewhat varies according to the oxygen concentration of an exhaust gas, the detected output may be corrected for the oxygen concentration, thereby further improving accuracy in measuring a combustible gas component concentration.

In this case, the oxygen concentration of an exhaust gas may be measured through use of a separately provided oxygen sensor. However, since the current flowing through the oxygen concentration adjustment pump element 3, i.e., an oxygen pump current IP, varies substantially linearly with the oxygen concentration of an exhaust gas, information regarding the oxygen concentration of an exhaust gas may be obtained from the pump current IP. This provides an advantage that there is no need for employing another oxygen sensor.

Figure 14:
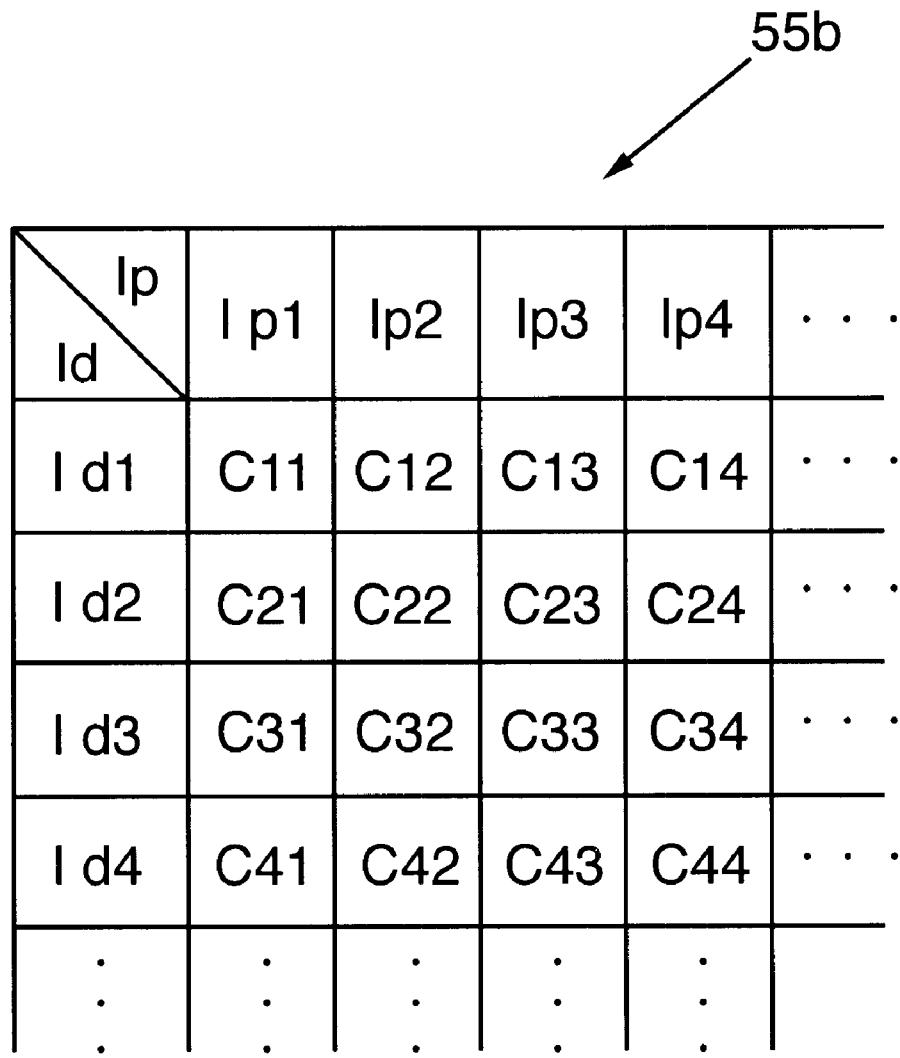
FIG. 14 is a view showing another example of a concentration conversion table.

Specifically, as shown in FIG. 9, a resistor 73 for current measurement use is provided on an output path of the differential amplifier 57. The pump current IP is detected by means of a differential amplifier 59 (including an operational amplifier 59a and peripheral resistors 59b to 59e) in the form of the difference between voltages as measured at both ends of the resistor 73. The thus-detected pump current IP is input to the microprocessor 52 via an A/D converter 74. As shown in FIG. 14, the concentration conversion table 55b of the ROM 55 assumes the form of a two-dimensional table and contains groups of values of combustible gas component concentration (for example, values of HC concentration) corresponding to values of detected current Id1, Id2, Id3, etc. of the combustible gas component concentration detection element 5. The groups of values of combustible gas component concentration are associated with various values of pump current IP (i.e., values of oxygen concentration). A combustible gas component concentration corresponding to a combination of a measured pump current IP and a measured output current Id is calculated with reference to the concentration conversion table 55b through two-dimensional interpolation. The thus-obtained value is output as a corrected combustible gas component concentration. In this case, the contents of the concentration conversion table 55b serve as information regarding the relation between an output current and a combustible gas component concentration, and the ROM 55 serves as a means for storing such information. The CPU 53 of the microprocessor 52 serves as the correction means.

In FIG. 9, in an ordinary state, the direction of the output current of the combustible gas component concentration detection element 5 (i.e., the current flowing between the second electrode 16 and the oxygen reference electrode 14) is such that oxygen is pumped out from the second processing space 10 or current flows from the oxygen reference electrode 14 to the second electrode 16. However, when the concentration of the combustible gas component introduced into the second processing space 10 becomes extremely high, oxygen in the second processing space 10 is consumed excessively due to combustion of the combustible gas component, and in some cases, the current flows in the reverse direction, depending on the concentration cell electromotive force generated in the combustible gas component concentration detection element 5.

Figure 15:
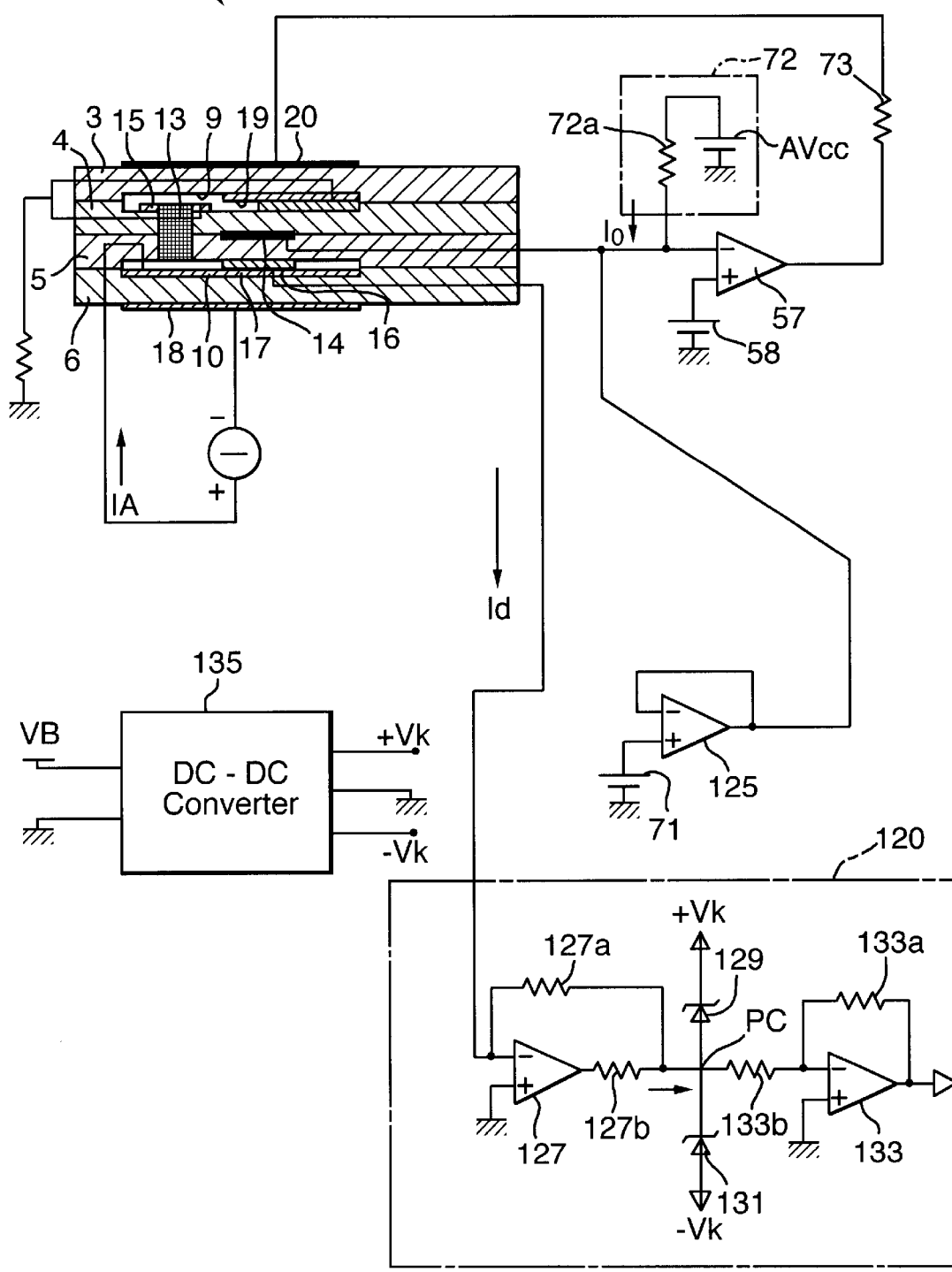
FIG. 15 is a circuit diagram showing an example of a sensor peripheral circuit having a current limit circuit.
Figure 16:
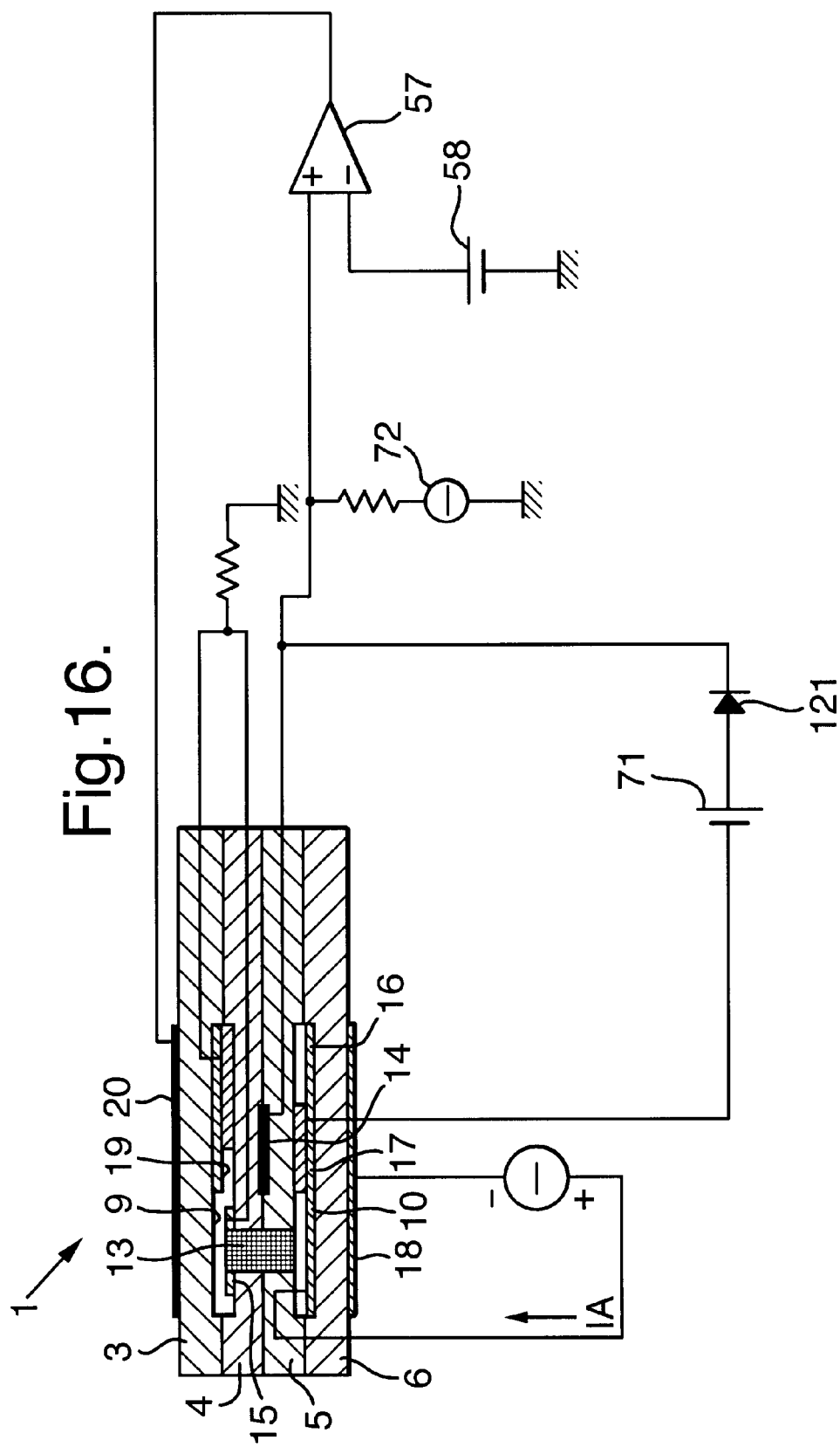
FIG. 16 is circuit diagram showing simplification of the current limit circuit effected through use of a diode.

This phenomenon will be described with reference to FIG. 15. The oxygen concentration within the second processing space 10 is always lower than that of the oxygen reference electrode 14. Thus, with the absolute value of a voltage of the power source 71 taken as VC and the absolute value of an oxygen concentration cell electromotive force of the combustible gas component concentration detection element 5 taken as Ea, Id varies with (VC—Ea). When VC is equal to Ea, Id becomes substantially zero. When the combustible gas component concentration of a gas flowing into the second processing space 10 increases with a resultant increase in the amount of oxygen to be consumed through combustion, the oxygen concentration cell electromotive force Ea increases. Id flows in a direction toward the oxygen reference electrode 14 (oxygen flows to the second electrode 16; the polarity of Id is defined as negative). By contrast, when the combustible gas component concentration decreases, the oxygen concentration cell electromotive force Ea decreases. Id flows in a direction toward the second electrode 16 (oxygen flows to the oxygen reference electrode 14; the polarity of Id is defined as positive).

In this case, the oxygen concentration cell element 4 and the combustible gas component concentration detection element 5 share the oxygen reference electrode 14, which is a self-generation-type reference electrode. Accordingly, when Id flows in the negative direction and its absolute value is excessively high (i.e., with a negative limit value taken as −Idn (Idn>0), Id<−Idn), a large amount of oxygen flows out from the oxygen reference electrode 14 into the second electrode 16. Thus, the oxygen reference electrode 14 fails to maintain an oxygen concentration required for serving as an oxygen reference electrode. As a result, the oxygen concentration cell element 4 fails to properly operate, and consequently control of the oxygen concentration within the first processing space 9 is disabled, resulting in an impairment in the detection accuracy of the sensor 1.

Meanwhile, when the concentration of hydrocarbon or a like component in exhaust gas from an internal combustion engine is to be detected, a fuel cut or a like operation (performed, for example, in order to prevent overheat of catalyst or to save fuel during deceleration with a throttle valve fully closed or in a like mode) may cause an excessive increase in the oxygen concentration of the exhaust gas to be measured. In this case, Id flows in the positive direction and its absolute value is excessively high (i.e., with a positive limit value taken as Idp (Idp>0), Id>Idp), and a large amount of oxygen flows into the oxygen reference electrode 14. Thus, the internal pressure of the oxygen reference electrode 14 becomes excessively large, causing a problem such as breakage of the electrode.

In order to avoid such problems, a current limit circuit is advantageously provided in a conductive passage extending between the combustible gas component concentration detection element 5 and the constant DC-voltage power source 71. The current limit circuit hinders a flow of Id falling outside the range "−Idn<Id<Idp." FIG. 15 shows an example of the current limit circuit (the same features as those of the circuit of FIG. 9 are denoted by common reference numerals, and their detailed description is omitted). In FIG. 15, the constant voltage VC from the constant DC-voltage power source 71 is applied via a voltage follower 125 such that the oxygen reference electrode 14 becomes positive. Also, a current limit circuit 120 is provided on a current output passage extending from the second electrode 16. The constant current power source 72 applies the source voltage AVcc to the oxygen concentration cell element 4 via a resistor 72a that has a sufficiently large resistance as compared to the internal resistance of the oxygen concentration cell element 4 at a sensor operation temperature (for example, 1000 to 5000 times the internal resistance). As a result, a substantially constant small current Io is applied to the oxygen concentration cell element 4 in such a direction that oxygen is pumped out from the first processing space 9 into the oxygen reference electrode 14.

In the current limit circuit 120, the current Id from the second electrode 16 is converted to a corresponding output voltage Vd at an operational amplifier 127. The operational amplifier 127, together with resistors 127a and 127b, constitutes a current-voltage conversion circuit (hereinafter, referred to as the current-voltage conversion circuit 127). The output voltage Vd is supplied to a voltage control point PC. Zener diodes 129 and 131 are connected to the voltage control point PC. Voltages Vk and −Vk (Vk>0) are applied to the Zener diodes 129 and 131, respectively. The Zener diodes 129 and 131 are selected so as to have Zener voltages (Vk+Vdn) and (Vk+Vdp) corresponding to current limits Idn and Idp, respectively. The voltages Vk and −Vk are generated through conversion of a car battery voltage VB by means of a DC—DC converter 135.

When a voltage at the control point PC is about to exceed Vdp (i.e., when the current Id is about to exceed Idp), the Zener diode 131 becomes conductive. Similarly, when the voltage at the control point PC is about to drop below −Vdn, the Zener diode 129 becomes conductive. Thus, the current Id is controlled so as to hold −Idn<Id<Idp.

When mere prevention of Id<−Idn suffices, the bidirectional current limit circuit 120 may be replaced with a unidirectional current limit circuit. When mere prevention of Id<0 (i.e., mere prevention of leakage of oxygen from the oxygen reference electrode 14 to the second electrode 16) suffices, the current limit circuit 120 may be replaced with a diode 121 for shutting off current of the corresponding direction.

Figure 17:
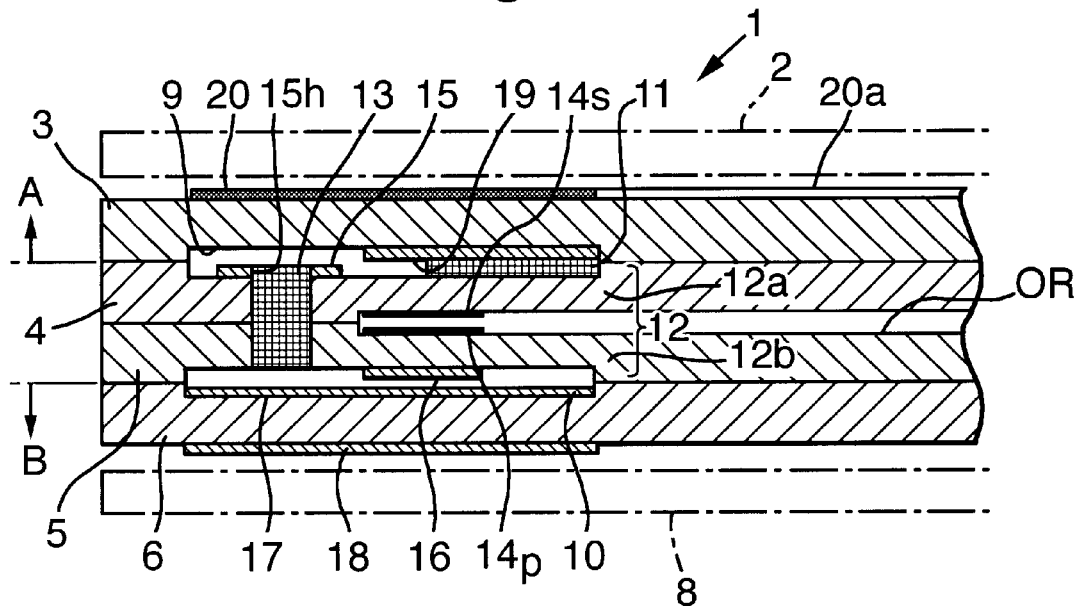
FIG. 17 is a sectional view showing a modification of the sensor of FIG. 1.
Figure 18:
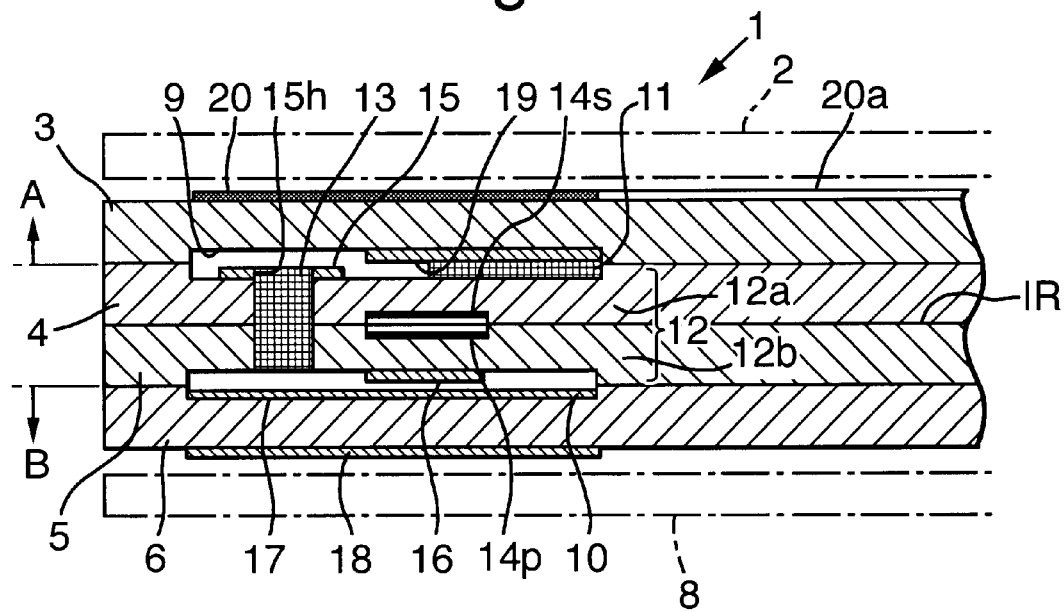
FIG. 18 is a sectional view showing another modification of the sensor of FIG. 1.

Also, insofar as the reference potential of the oxygen reference electrode 14 (or the oxygen concentration of the gas held in the voids of the oxygen reference electrode 14) is maintained in a range that grantees proper measurement, the polarity of application of VC may be set opposite that of the above-described case, i.e., such that oxygen is pumped from the oxygen reference electrode 14 into the second processing space 10. The oxygen reference electrode 14 is a self-generation-type electrode embedded in the partition wall 12. However, for example, as shown in FIG. 17, a reference space OR, into which the atmosphere serving as a reference gas is introduced via an atmosphere communication portion, is provided in the partition wall 12. On the inner surfaces of the reference space OR may be provided an oxygen reference electrode 14s associated with the oxygen concentration cell element 3, and an oxygen reference electrode 14p associated with the combustible gas component concentration detection element 5. Alternatively, as shown in FIG. 18, a self-generation-type oxygen reference electrodes 14s and 14p respectively corresponding to the oxygen concentration cell element 3 and the combustible gas component concentration detection element 5 may be embedded in the wall partition 12 such that the electrodes 14s and 14p are isolated from each other by means of, for example, an insulating layer IR mainly composed of alumina or the like. In these cases, the polarity of applied VC may be set such that oxygen is pumped out from the second processing space 10 into the oxygen reference electrode 14 or such that oxygen is pumped out from the oxygen reference electrode 14 into the second processing space 10.

TEST EXAMPLE 1

In the gas sensor 1 shown in FIG. 1, the elements 3 to 6 were formed through use of a $ZrO_2$ solid electrolyte which contains $Y_2O_3$ in an amount of 5% by weight. The porous electrodes 14 to 18, and 20 were formed through use of a Pt—Au (1% by weight) alloy. The fourth electrode 19 was a two-layer electrode composed of the main electrode layer 151 (FIG. 6) and the surface electrode layer 152. The main electrode layer 151 was integrally formed with the pump cell unit 111 through use of a Pt—Au (1% by weight) alloy and through firing. Au paste was applied onto the main electrode layer 151, followed by secondary firing (at 900° C.) to thereby form the surface electrode layer 152. The first processing space 9 and the second processing space 10 each had a height of 0.02 mm, a width of 22 mm, and a length of 7 mm. A section was taken across the thickness of the fourth electrode 19. The section was analyzed for composition through use of an Electron Probe Micro Analyzer (EPMA; energy diffusion system). As a result, it was found that the Au content (WAu) of the fourth electrode 19 at the main electrode portion is 4.1% by weight, and the Pt content of the fourth electrode 19 at the main electrode portion is 95.9% by weight. Also, an Au rich layer was found at the surface.

Meanwhile, there was prepared a test gas which contained oxygen (1% or 7%), water vapor (10%), carbon dioxide (10%), one of the below-described hydrocarbons, which serves as a combustible gas component (in an amount within the below-described ranges), and nitrogen (balance).

Concentration ranges of hydrocarbons:

$CH_4$ (methane): 0–400 ppmC
$C_2H_6$ (ethane): 0–600 ppmC
$C_3H_8$ (propane): 0–2000 ppmC
i-$C_4H_{10}$ (isobutane): 0–1200 ppmC (ppmC: parts per million represented with carbon equivalent). The sensor 1 was incorporated into the gas sensor system 50 of FIG. 9. The sensor 1 was held in the test gas and heated by the heaters 2 and 8 so as to heat the elements 3 to 6 to a temperature of 750° C. The temperature of the test gas was 300° C., and the flow rate was 15 liters/min. Throughout the examples, the test gas was analyzed by use of a flame ionized detector (for measurement of an amount of HC), a magnetic pneumatic analyzer (for measurement of an amount of oxygen), a nondispersive infrared absorption analyzer (for measurement of an amount of carbon dioxide (or for measurement of an amount of carbon monoxide in an experiment described below)), and a chemical luminescence detector (for measurement of an amount of nitrogen monoxide).

Figure 19:
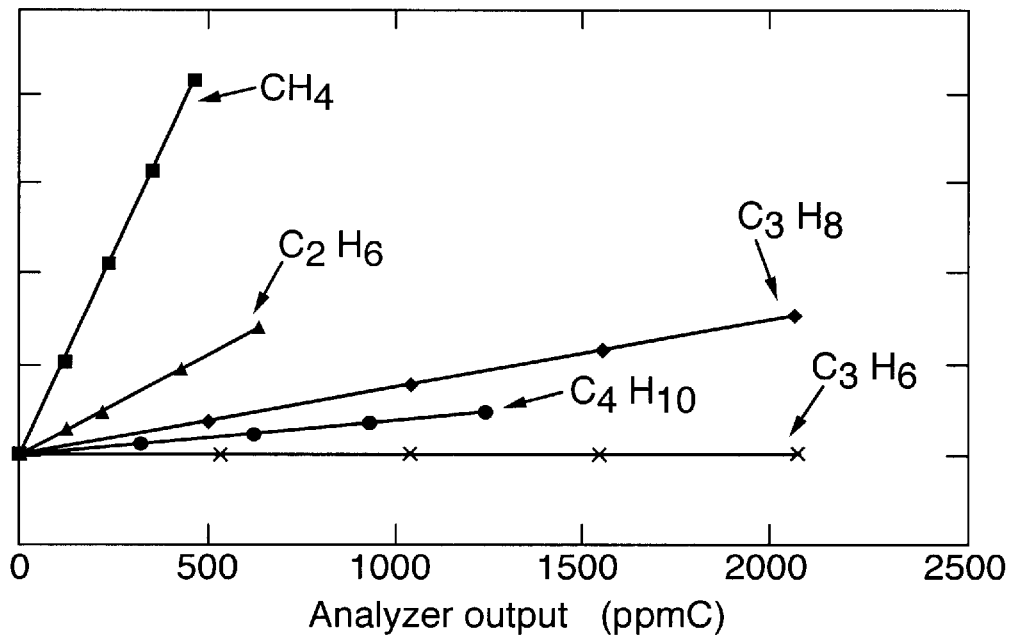
FIG. 19 is a graph showing the dependency of the sensor output on the concentration of each HC obtained in the experiment of Test example 1 in which the gas sensor of the present invention was used (oxygen concentration: 1%)
Figure 20:
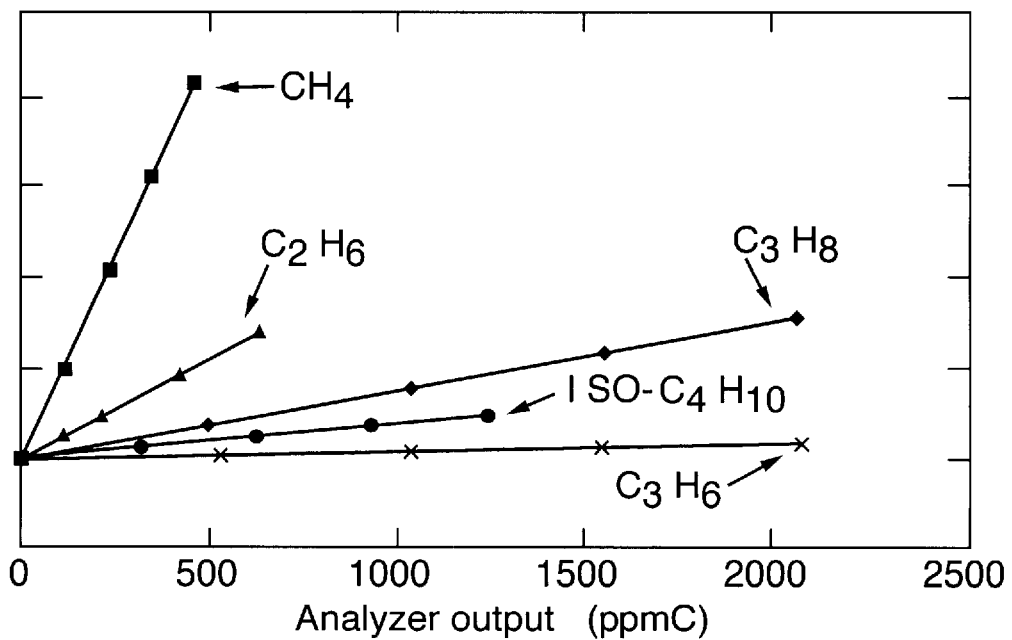
FIG. 20 is a graph showing the dependency of the sensor output on the concentration of each HC obtained in the experiment of Test example 1 in which the gas sensor of the present invention was used (oxygen concentration: 7%)

In this state, the target electromotive force EC of the oxygen concentration cell element 4 of the gas sensor 1 was set to such a value (approximately 550 mV) that the target oxygen concentration PX of the first processing space 9 becomes $10^{-11}$ atm. Under the setting conditions, the sensor system 50 was operated. It was examined how the output current Id of the combustible gas component concentration detection element 5 varies with the methane concentration of the test gas. Notably, the constant voltage DC power source 58 (FIG. 9) applied a voltage VC of 350 mV to the combustible gas component concentration detection element 5, and the constant current power source 80 supplied a current of 15 μA to the measurement-purpose-oxygen supply pump element 6. The results are shown in FIG. 19. As seen from FIG. 19, the output current Id of the gas sensor 1 changes linearly with the concentration of any hydrocarbon, indicating that the sensor 1 exhibits good detection performance. Especially, the sensor 1 has a high sensitivity for methane. FIG. 20 shows the results when the oxygen concentration was set to 7%. In this case as well, the sensor 1 exhibits good detection performance, and is not affected very much by oxide concentration.

Figure 30A:
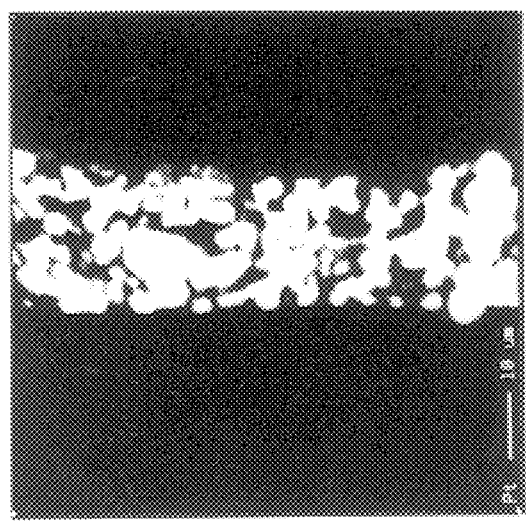
FIG. 30 shows EPMA characteristic-X-ray images of Pr, Au, and Zr of a cross section of the fourth electrode of the sensor used in Test example 1 (before aging)
Figure 30B:
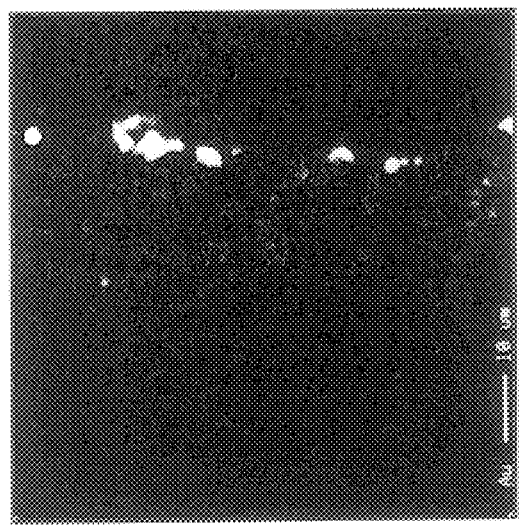
Figure 30C:
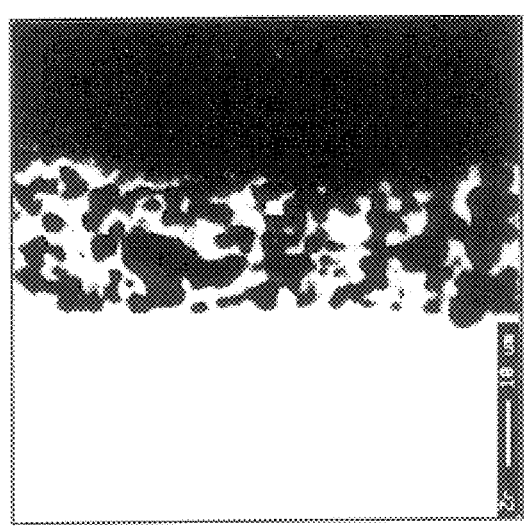

A section of the fourth electrode which was not used yet after secondary firing was examined through use of EPMA attached to SEM. FIG. 30 shows characteristic X-ray images (about 1000 magnifications) of the section corresponding to Pt (FIG. 30(a)), Au (FIG. 30(b)), and Zr (FIG. 30(c)). In the images shown in FIG. 30, a brighter portion indicates a higher characteristic X-ray intensity (i.e., element concentration). As seen from comparison of images between FIG. 30(a) and FIG. 30(c), a porous main electrode layer of Pt is formed as thick as about 20 μm on a solid electrolyte layer mainly composed of $ZrO_2$. In order to improve the bonding strength of the electrode through reduction of the difference of thermal expansion coefficient between the porous electrode and the solid electrolyte layer, Pt paste blended with $ZrO_2$ powder was used as an electrode material. Thus, a region of distribution associated with characteristic X-ray of Zr is observed in the main electrode layer. As seen from comparison of images between FIG. 30(a) and FIG. 30(b), a surface electrode layer mainly composed of Au is formed in an outermost surface layer portion of the main electrode layer. Notably, a thin dispersion of characteristic X-ray of Au is observed in a region corresponding to the main electrode layer. A conceivable reason is that Au diffused from the surface electrode layer side to the main electrode layer side during secondary firing.

Figure 31A:
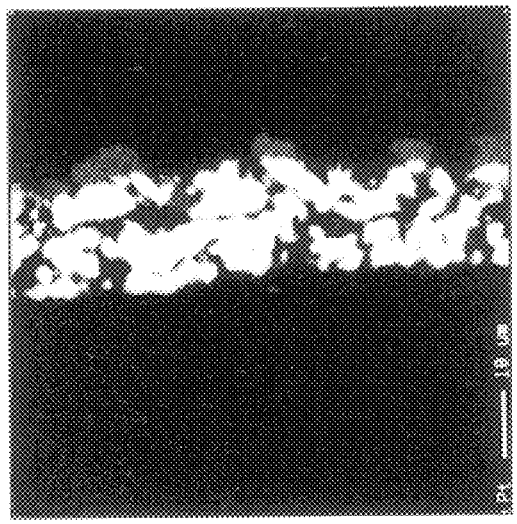
FIG. 31 shows EPMA characteristic-X-ray images of Pr, Au, and Zr of a cross section of the fourth electrode of the sensor used in Test example 1 (after aging).
Figure 31B:
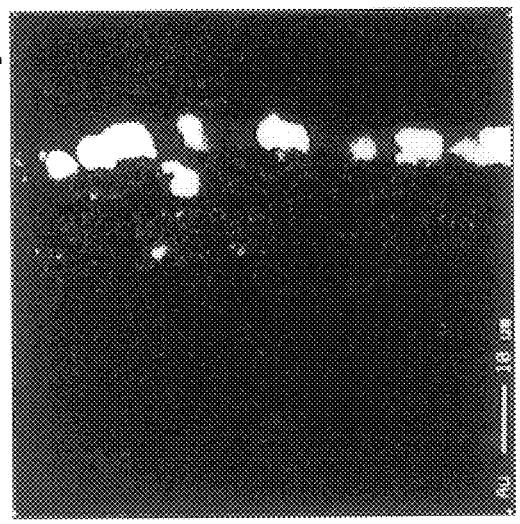
Figure 31C:
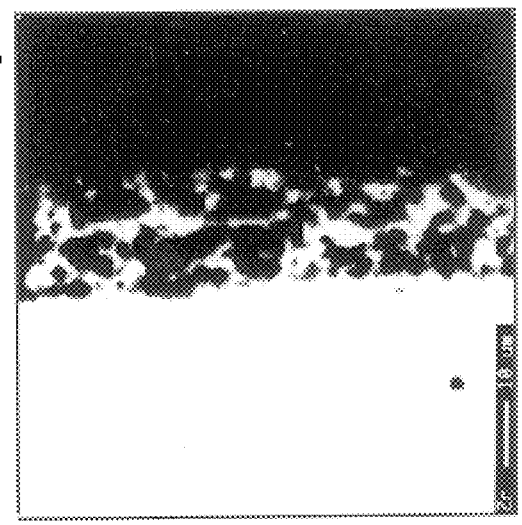

Next, the sensor was aged for 500 hours at 780° C. in the atmosphere. Subsequently, the section of the fourth electrode was subjected to examination through use of EPMA. FIG. 31 shows characteristic X-ray images (about 1000 magnifications) of the section corresponding to Pt (FIG. 31(*a*)), Au (FIG. 31(*b*)), and Zr (FIG. 31(*c*)). As compared to FIG. 23, a surface electrode layer region having a high Au concentration is wider, and the Pt concentration of the region is higher. Acceding to an Au—Pt equilibrium phase diagram, at 780° C., the solid-solution limit of Pt on the Au side is as high as about 20% by weight, while the solid-solution limit of Au on the Pt side is as low as about 5% by weight. In the main electrode layer, secondary firing highly conceivably caused an increase in the Au concentration in the vicinity of an interface with the surface electrode layer to near a saturation concentration in Pt. Accordingly, the above-mentioned aging conceivably causes the following tendency: diffusion of Au from the surface electrode layer side to the main electrode layer side is relatively difficult, while diffusion of Pt from the main electrode layer side to the surface electrode layer side relatively easily progresses.

As a result, diffusion of Pt to the surface electrode layer side conceivably advanced having priority over diffusion of Au to the main electrode layer side, resulting in expansion of the surface electrode layer region. As a result of this aging, the Pt concentration of the surface electrode layer increases to about a solid-solution limit of Pt in Au (for example, 20% by weight at 780° C.). However, up to this level of the Pt concentration does not affect the effect of the surface electrode layer for suppressing the catalytic activity for combustion. Also, a small time-course variation in the Pt concentration of the surface electrode layer during the sensor being used may advantageously improve the time-course stability of sensor characteristics (for example, an offset electromotive force of the oxygen concentration cell element). In this case, it is desirable to positively age the sensor in the above manner before shipment so as to sufficiently diffuse Pt to the surface electrode layer side.

The following reference experiment was performed. There was fabricated a sensor (Example sensor B) having the same structure as in Test example 1 except that the electrodes 15 and 16 were formed of a Pt—Au (1% by weight) porous alloy, and other electrodes were formed of Pt and were porous, and a sensor (Example sensor A) having the same structure as in Test example 1 except that the fourth electrode was formed to have a two-layer structure. Each of the sensor was operated under the same conditions except that a test gas contained oxygen (7%), water vapor (10%), carbon dioxide (10%), nitrogen monoxide (500 ppm), methane serving as a combustible gas component (200 ppmC), and nitrogen (balance), and the sensor output was examined. Whereas the output current Id of Example sensor B was about 1 $\mu$A, the output current Id of Example sensor A was about 4 $\mu$A. Therefore, Example sensor A has a higher sensitivity. A conceivable reason for this is that the two-layer structure of the fourth electrode 19 decreases the catalytic activity for combustion of methane, so that combustion loss of methane within the first processing space 9 decreases.

TEST EXAMPLE 2

Figure 21:
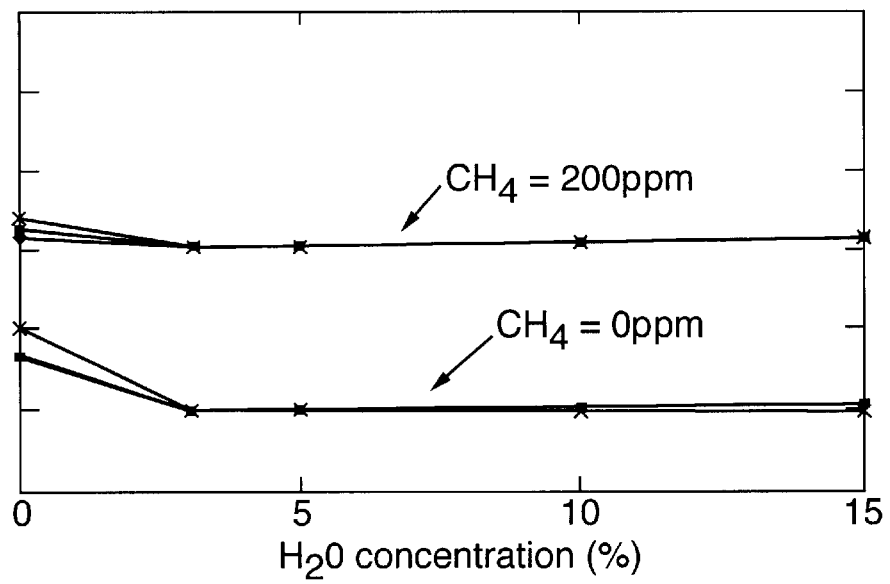
FIG. 21 is a graph showing an influence, on the sensor output, of water vapor concentration obtained in the experiment in Test example 2.

The experiment similar to that performed in Test example 1 was performed under the same conditions except that a test gas contained methane (0 or 200 ppmC), oxygen (1%), water vapor (0–15%), carbon dioxide (10%), and nitrogen (balance). The results are shown in FIG. 21. Specifically, the output current Id is generally stable for any water vapor concentration. Especially, when the water vapor concentration falls in the range of 3–15%, the output current hardly changes regardless where methane is present or absent. This indicates that in the gas sensor 1, decomposition of water vapor is hardly initiated during measurement, and thus a methane concentration is stably obtained regardless of the water vapor concentration.

TEST EXAMPLE 3

The same gas sensor system 50 as used in Test example 1 was used. The sensor 1 was held in a test gas composed of methane (0 or 200 ppmC), oxygen (1%), water vapor (3–15%), carbon dioxide (10%), and nitrogen (balance). The sensor 1 was heated by the heaters 2 and 8 so as to heat the elements 3 to 6 to a temperature of 650° C. In the gas sensor 1, the target electromotive force EC of the oxygen concentration cell element 4 was set to such various values that the target oxygen concentration PX of the first processing space 9 became $10^{-15}$ atm to $10^{-5}$ atm. Under the setting conditions, the sensor system 50 was operated, and the output current Id of the oxygen concentration adjustment pump element 5 was measured. Notably, the constant voltage DC power source 58 (FIG. 9) applied a voltage VC of 350 mV to the combustible gas component concentration detection element 5, and the constant current power source 80 supplied a current of 15 $\mu$A to the measurement-purpose-oxygen supply pump element 6.

Figure 22:
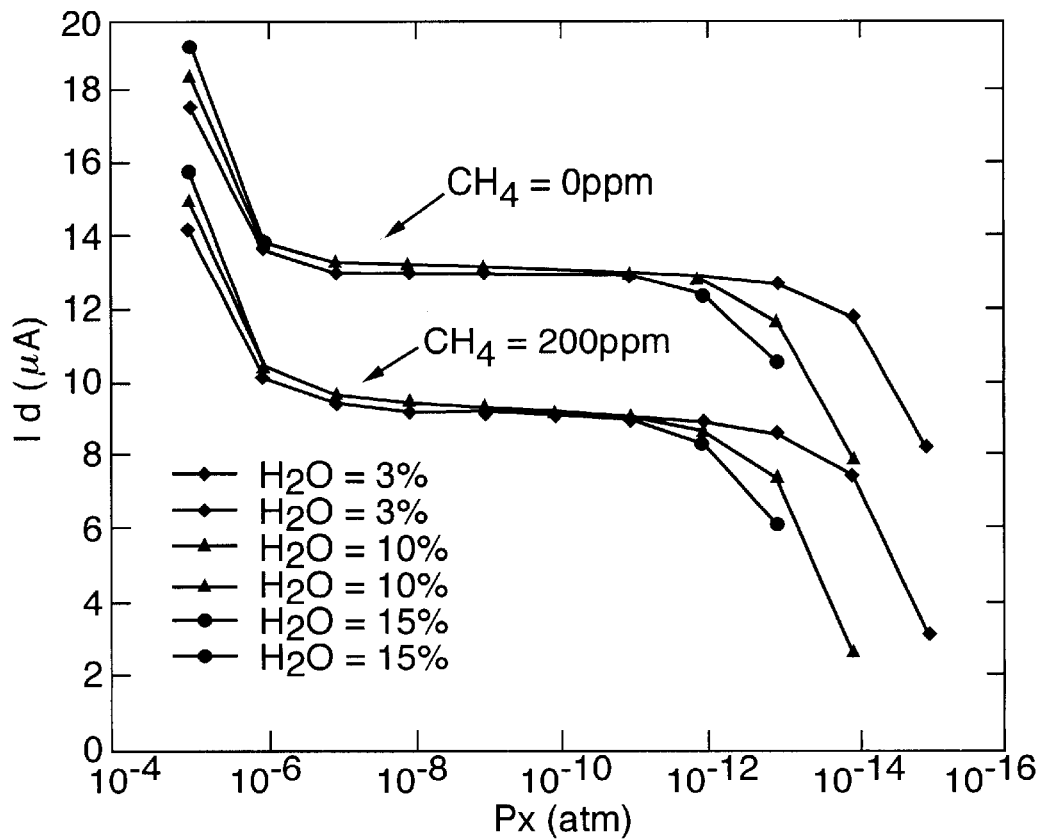
FIG. 22 is a graph showing an influence, on the sensor output, of the setting value for oxygen concentration in the first processing space obtained in the experiment in Test example 3.

FIG. 22 shows the relationship between Id and PX with methane concentrations taken as parameters. As seen from FIG. 22, at a PX value of $10^{-12}$ atm to $10^{-6}$ atm, a substantially constant sensor output is obtained irrespective of the PX value for any of the methane concentrations. At a PX value of $10^{-12}$ atm or lower, Id, which is expected to be constant, shows a sharp decrease (i.e., an increase in apparent combustible gas component concentration). A conceivable reason for this is that a large amount of hydrogen, which is a combustible gas component, was generated as a result of decomposition of water vapor, and oxygen was consumed in the second processing space. At a PX value of $10^{-6}$ atm or higher, Id shows a sharp increase. A conceivable reason for this is that the amount of oxygen remaining unpumped increases quickly. Further, there is a tendency that the sensitivity $\Delta$Id for methane decreases as the value of PX increases within the range of $10^{-12}$ atm to $10^{-6}$ atm. A conceivable reason for this is that methane was burned within the first processing space, i.e., the methane concentration reduced, due to an excessive oxygen concentration.

TEST EXAMPLE 4

Figure 23:
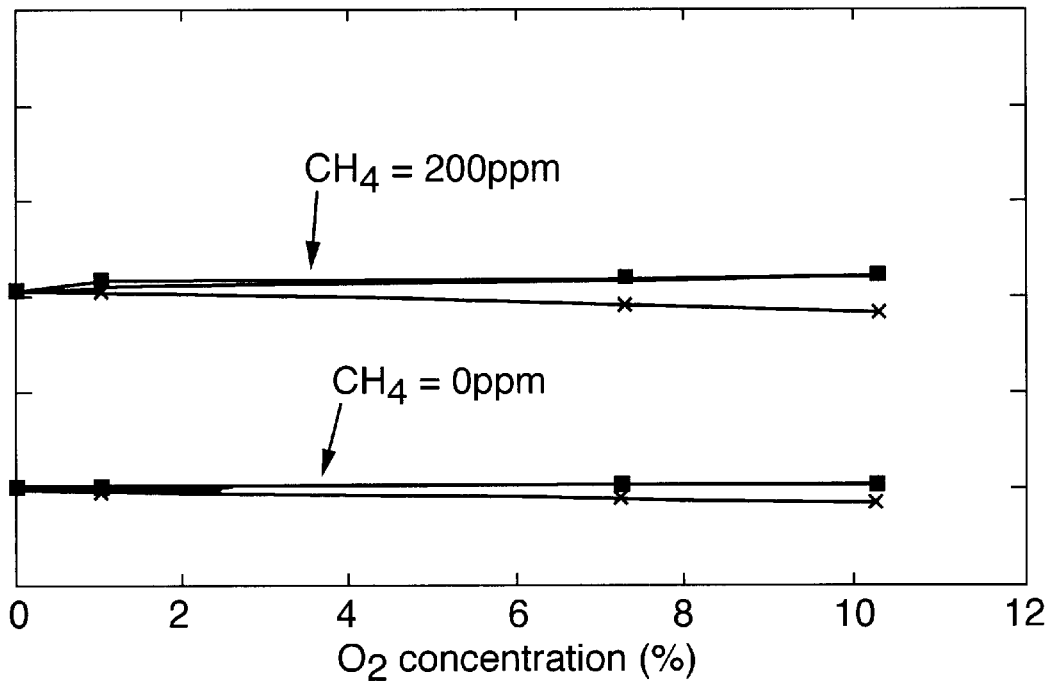
FIG. 23 is a graph showing an influence, on the sensor output, of the oxygen concentration of a test gas obtained in the experiment in Test example 4.

The experiment similar to that performed in Test example 1 was performed under the same conditions except that a test gas contained methane (0 or 200 ppmC), oxygen (0–10%), water vapor (10%), carbon dioxide (10%), and nitrogen (balance). The results are shown in FIG. 23. Specifically, the output current Id corresponding to either methane concentration hardly changes regardless of change in oxygen concentration. This indicates that in the gas sensor 1, a methane concentration is stably obtained regardless of the oxygen concentration of the measurement gas.

TEST EXAMPLE 5

Figure 24:
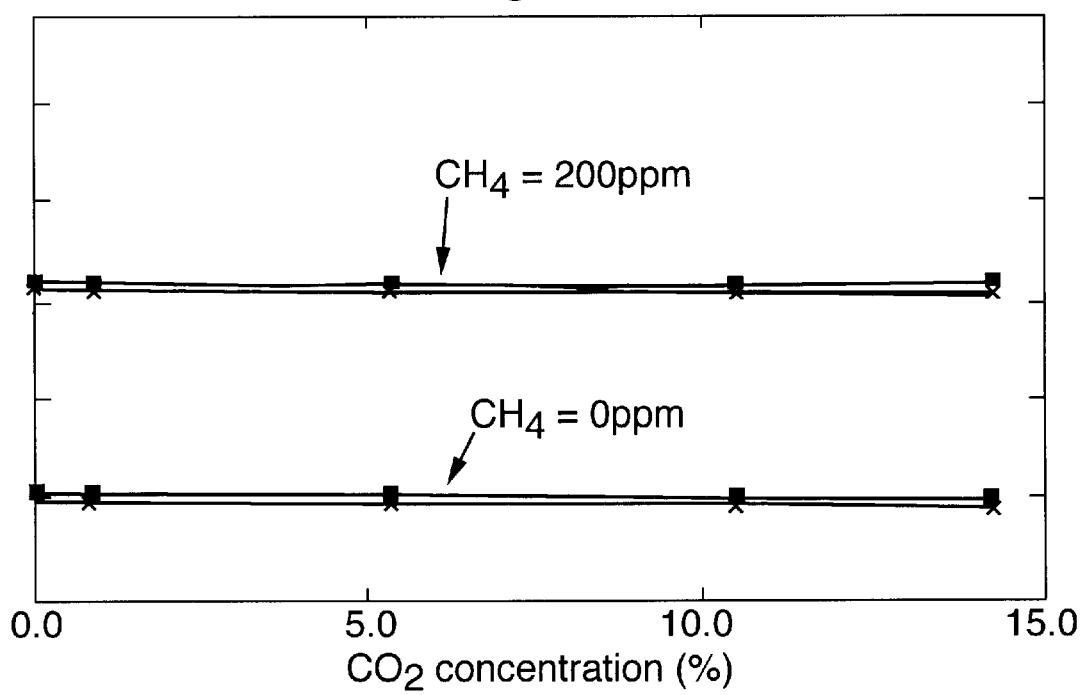
FIG. 24 is a graph showing an influence, on the sensor output, of the carbon dioxide concentration of a test gas obtained in the experiment in Test example 5.

The experiment similar to that performed in Test example 1 was performed under the same conditions except that a test gas contained methane (0 or 200 ppmC), oxygen (1%), water vapor (10%), carbon dioxide (0–15%), and nitrogen (balance). The results are shown in FIG. 24. The output current Id corresponding to either methane concentration hardly changes regardless of change in carbon dioxide concentration. This indicates that the gas sensor 1 is hardly affected by the concentration of carbon dioxide.

TEST EXAMPLE 6

Figure 25:
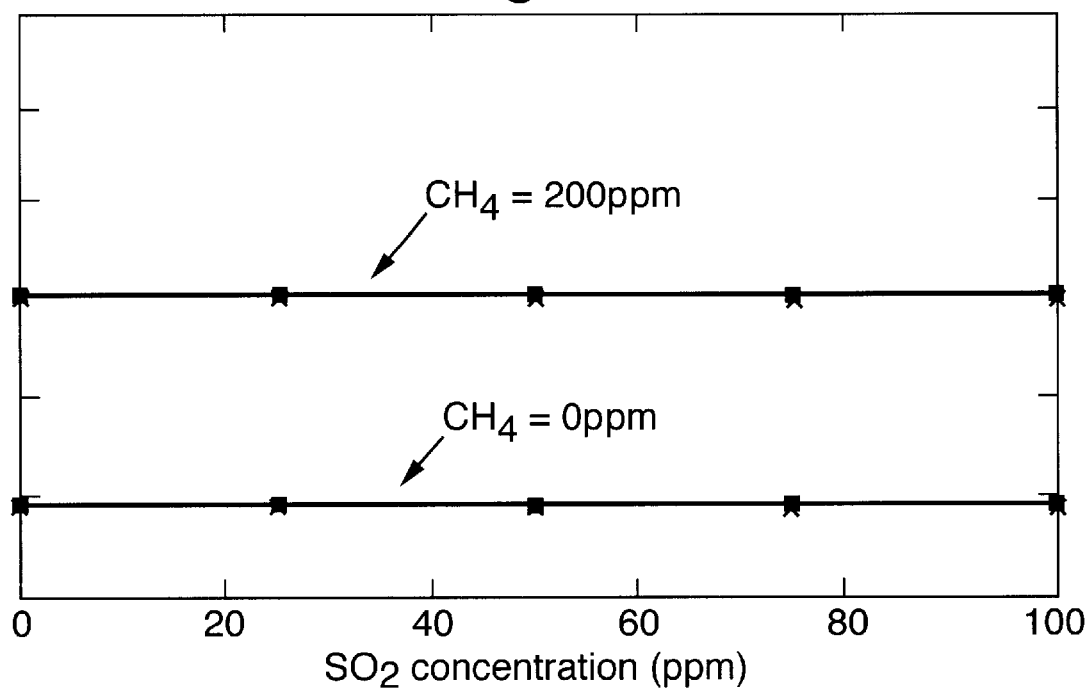
FIG. 25 is a graph showing an influence, on the sensor output, of the sulfur oxide concentration of a test gas obtained in the experiment in Test example 6.

The experiment similar to that performed in Test example 1 was performed under the same conditions except that a test gas contained methane (0 or 200 ppmC), oxygen (1%), water vapor (10%), carbon dioxide (10%), sulfur dioxide (0–100 ppm), and nitrogen (balance). The results are shown in FIG. 25. The output current Id corresponding to either methane concentration hardly changes regardless of change in sulfur dioxide concentration. This indicates that the gas sensor 1 is hardly affected by the concentration of sulfur dioxide.

TEST EXAMPLE 7

Figure 26:
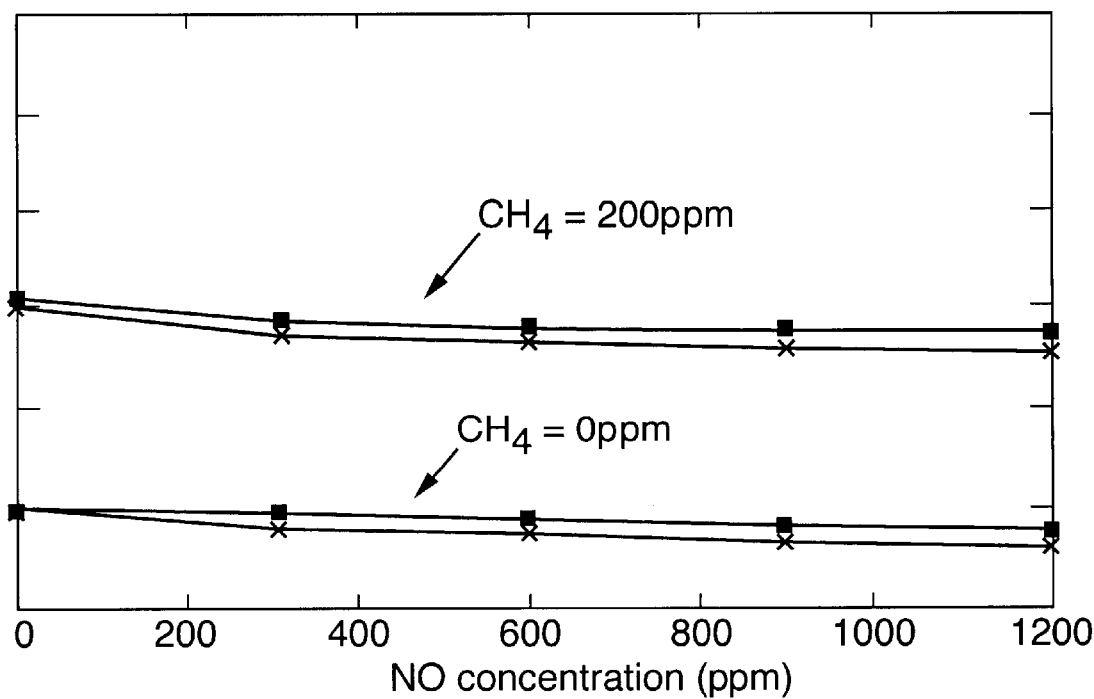
FIG. 26 is a graph showing an influence, on the sensor output, of the nitrogen monoxide concentration of a test gas obtained in the experiment in Test example 7.

The experiment similar to that performed in Test example 1 was performed under the same conditions except that a test gas contained methane (0 or 200 ppmC), oxygen (1%), water vapor (10%), carbon dioxide (10%), nitrogen monoxide (0–1200 ppm), and nitrogen (balance). The results are shown in FIG. 26. The output current Id corresponding to either methane concentration hardly changes regardless of change in nitrogen monoxide concentration. This indicates that the gas sensor 1 is hardly affected by the concentration of nitrogen monoxide.

TEST EXAMPLE 8

Figure 27:
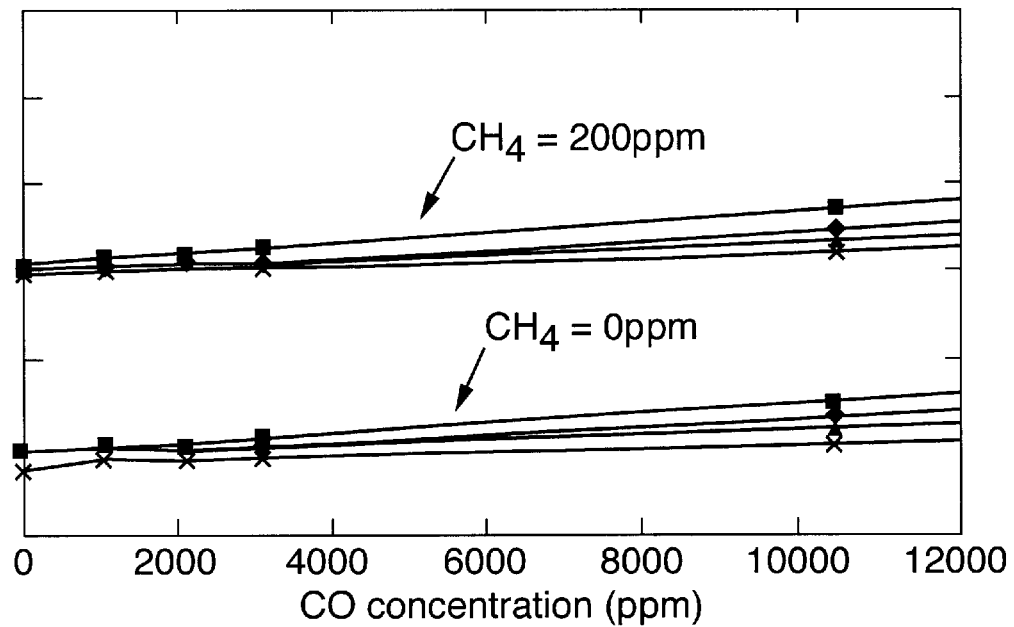
FIG. 27 is a graph showing an influence, on the sensor output, of the carbon monoxide concentration of a test gas obtained in the experiment in Test example 8.

The experiment similar to that performed in Test example 1 was performed under the same conditions except that a test gas contained methane (0 or 200 ppmC), oxygen (1%), water vapor (10%), carbon dioxide (10%), carbon monoxide (0–12000 ppm), and nitrogen (balance). The results are shown in FIG. 27. When carbon monoxide concentration is not greater than 3000 ppm, the output current Id corresponding to either methane concentration hardly changes regardless of change in carbon monoxide concentration, which indicates that the gas sensor 1 is hardly affected by carbon monoxide concentration. When carbon monoxide concentration is greater than 3000 ppm, the sensor output changes slightly, but is stable generally. Although carbon monoxide is a combustible gas component, the influence of carbon monoxide on the output obtained as a result of detection of methane is small up to a concentration as high as 12000 ppm. This indicates that an excellent selectivity is obtained in detecting methane even when carbon monoxide coexists. A conceivable reason for this is that carbon monoxide is burned more readily than is methane in the first processing space, while the first electrode, for example, serves as a catalyst.

Figure 28:
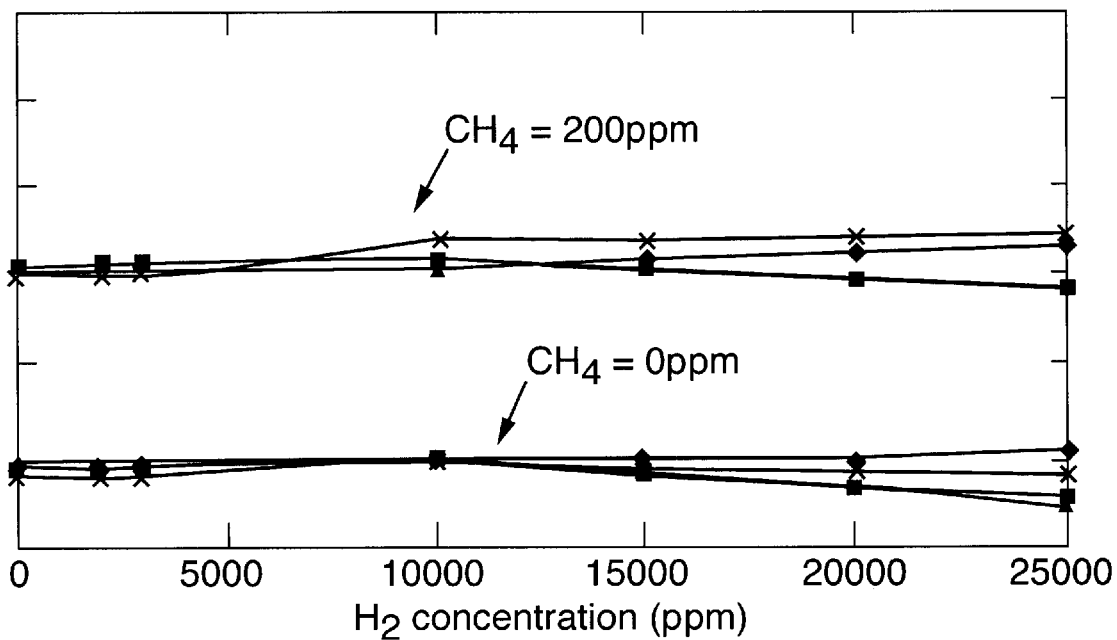
FIG. 28 is a graph showing an influence, on the sensor output, of the hydrogen concentration of a test gas obtained in the experiment in Test example 8.
Figure 29:
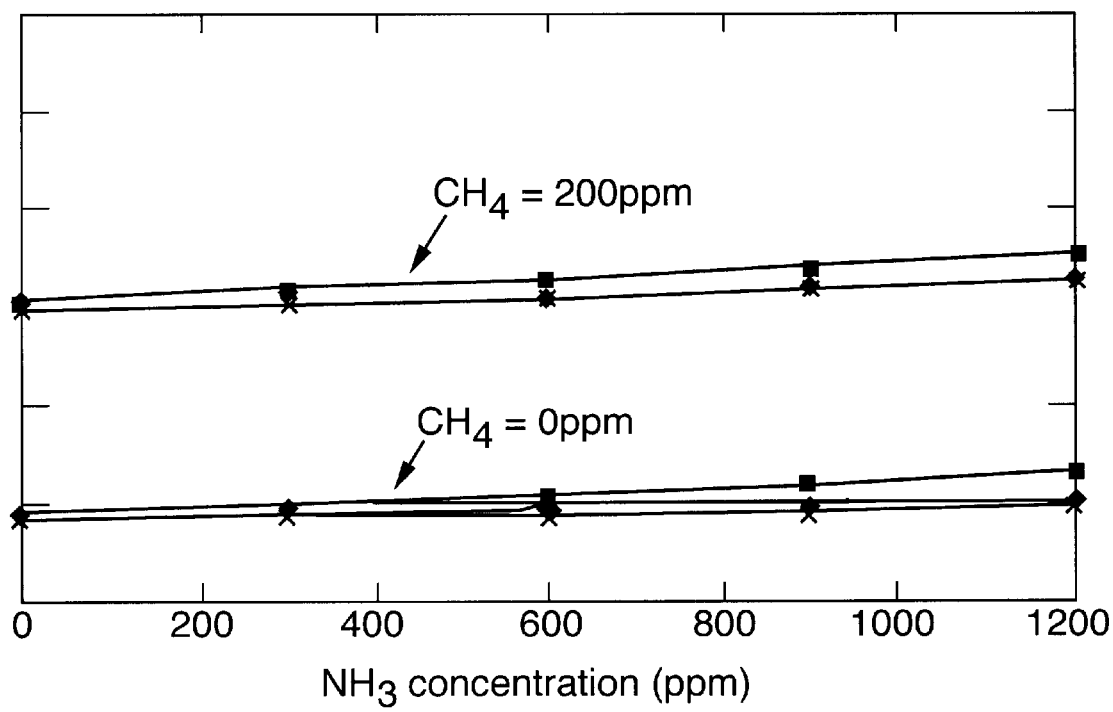
FIG. 29 is a graph showing an influence, on the sensor output, of the ammonia concentration of a test gas obtained in the experiment in Test example 8.

FIGS. 28 and 29 show the results of experiments in which hydrogen or ammonia was used in place of carbon monoxide. The results indicate that even when hydrogen or ammonia coexists as a combustible gas component, the sensor output for methane is hardly affected thereby, and the sensor exhibits an excellent performance for selective detection.

What is claimed is:

1. A gas sensor comprising:
  a first processing space and a first gas passage for introducing a measurement gas into said first processing space;
  a second processing space and a second gas passage for introducing a gas contained in said first processing space into said second processing space;
  an oxygen concentration detection element for measuring the oxygen concentration of the gas contained in said first processing space;
  a first oxygen pump means for pumping out oxygen from said first processing space or pumping oxygen into said first processing space so as to adjust to a predetermined level the oxygen concentration of the measurement gas introduced into said first processing space, which is measured by said oxygen concentration detection element;
  a second oxygen pump means for pumping into said second processing space a constant amount of oxygen for measuring the combustible gas component contained in the measurement gas; and
  a combustible gas component concentration detection means for pumping out oxygen from said second processing space under a constant applied voltage, so that a current output from said combustible gas component concentration detection element varies inversely to the amount of oxygen consumed by combustion of the combustible gas component contained in the gas introduced from said first processing space into said second processing space to thereby provide information regarding a detected concentration of the combustible gas component of the measurement gas, and
  at least one of said combustible gas component concentration detection means and second oxygen pump means comprises an oxidation catalyst exposed to said second processing space for accelerating combustion of a combustible gas component contained in the gas which has been introduced into said second processing space from said first processing space via the second gas passage.

2. A gas sensor according to claim 1, wherein said first oxygen pump means comprises means for adjusting the oxygen concentration of the measurement gas introduced into said first processing space, which is detected by said oxygen concentration detection element, such that the oxygen concentration falls within such a range that a reaction of decomposing water vapor contained in the measurement gas is not substantially initiated.

3. A gas sensor according to claim 1, wherein said first oxygen pump means comprises means for adjusting the oxygen concentration of the measurement gas introduced into said first processing space, which is detected by said oxygen concentration detection element, such that the oxygen concentration falls within a range of $10^{-12}$ atm to $10^{-6}$ atm.

4. A gas sensor according to claim 1, wherein said first oxygen pump means comprises means for adjusting the oxygen concentration of the measurement gas in said first processing space detected by said oxygen concentration detection element such that the oxygen concentration falls within a range in which components having combustion activities higher than that of hydrocarbon to be detected are burned more readily than is hydrocarbon to be detected.

5. A gas sensor according to claim 1, wherein said oxygen concentration detection element is an oxygen concentration cell element formed of a first oxygen-ion-conductive solid electrolyte having electrodes formed on both surfaces thereof including a first electrode exposed to said first processing space, said combustible gas component concentration detection means comprising a second oxygen-ion-conductive solid electrolyte having electrodes formed on both surfaces thereof including a second electrode exposed to said second processing space, said second oxygen pump means comprising a third oxygen-ion-conductive solid electrolyte having electrodes formed on both surfaces thereof including a third electrode exposed to said second processing space, and said first oxygen pump means comprising a fourth oxygen-ion-conductive solid electrolyte having electrodes formed on both surfaces thereof including a fourth electrode exposed to said first processing space;

each of: the first, second, third and fourth electrodes is in the form of a porous electrode having oxygen molecule dissociating capability, at least one of the second and third electrodes having catalytic activity for oxidation of the combustible gas component contained in the measurement gas; and the oxidation catalytic activities of the first through fourth electrodes are selected such that an amount of oxygen consumed in said second processing space due to combustion of the combustible gas component becomes greater than that in said first processing space.

6. A gas sensor according to claim 5, wherein said first processing space and said second processing space are arranged with a partition wall, formed of an oxygen-ion-conductive solid electrolyte, disposed therebetween;

the second gas passage is formed in the partition wall so as to establish communication between said first processing space and said second processing space, an oxygen reference electrode being embedded in the partition wall at a thicknesswise intermediate portion;

the first electrode is formed on the partition wall in such a manner as to be exposed to said first processing space, the first electrode, the oxygen reference electrode, and a portion of the partition wall interposed between the first electrode and the oxygen reference electrode constituting said oxygen concentration cell element;

the second electrode is formed on the partition wall in such a manner as to be exposed to said second processing space, the second electrode, the oxygen reference electrode, and a portion of the partition wall interposed between the second electrode and the oxygen reference electrode constituting said combustible gas component concentration detection element; and said second oxygen pump means is disposed opposite the partition wall with said second processing space disposed therebetween.

7. A gas sensor according to claim 6, wherein at least one of the oxygen reference electrode and the second electrode is formed at a position that does not interfere with the second gas passage.

8. A gas sensor according to claim 1, wherein said combustible gas component concentration detection means comprises a second oxygen-ion-conductive solid electrolyte having electrodes formed on both surfaces thereof including an electrode exposed to said second processing space formed at a position that does not interfere with the second gas passage.

9. A gas sensor according to claim 1, wherein said first oxygen pump means comprises an oxygen-ion-conductive solid electrolyte having electrodes formed on both surfaces thereof including an electrode referred to as a fourth electrode exposed to said first processing space;

the fourth electrode is formed of:
      a porous main electrode layer made of Pt—Au alloy or Pt; and a porous surface electrode layer covering the main electrode layer to thereby form a surface layer portion of the fourth electrode, the surface electrode layer being made of a material selected from the group consisting of a metal containing Au or Ag as a main component, Pt—Au alloy, Au—Pd alloy, Pt—Ag alloy, and Pt—Ni alloy.

10. A gas sensor according to claim 9, wherein the fourth electrode has a two-layer structure comprising:

a porous main electrode layer made of Pt—Au alloy or Pt; and a porous surface electrode layer covering the main electrode layer to thereby form a surface layer portion of the fourth electrode, the surface electrode layer being made of an Au-containing metal that contains Au as a main component.

11. A method of manufacturing a gas sensor of claim 10, said method comprising:

a substrate electrode layer forming step in which a substrate electrode pattern containing an unfired layer of material powder for the main electrode layer of the fourth electrode is formed on an unfired compact of the oxygen-ion-conductive solid electrolyte layer contained in said first oxygen pump means, and the unfired main electrode layer is integrally fired with the unfired solid electrolyte compact to form on the oxygen-ion-conductive solid electrolyte layer a substrate electrode layer containing the main electrode layer; and a surface electrode layer forming step in which a layer of material powder for the surface electrode layer is formed on the substrate electrode layer, and is subjected to a secondary firing at a temperature lower than that in the integral firing to thereby form the surface electrode layer.

12. A manufacturing method according to claim 11, wherein said gas sensor is such that a pump cell unit including said first oxygen pump means is formed separately from a sensor cell unit including said oxygen concentration detection element, said second processing space, said combustible gas component concentration detection means, and said second oxygen pump means; and said pump cell unit and said sensor cell unit are joined together via a bonding material; and said method comprising the steps of:
      manufacturing said pump cell unit through firing such that the substrate electrode layer is formed without formation of the surface electrode layer;
      performing the secondary firing to form the surface electrode layer on the substrate electrode layer of said pump cell unit; and
      integrating said pump cell unit with said sensor cell unit, which has been separately manufactured through firing.

13. A gas sensor according to claim 9, wherein said oxygen concentration detection element comprises an oxygen-ion-conductive solid electrolyte having electrodes formed on both surfaces thereof including an electrode referred to as a first electrode exposed to said first processing space;

the first electrode is formed of a porous metal of Pt—Au alloy, Pt—Ag alloy, or Pt, and wherein the area of the first electrode is smaller than that of the fourth electrode.

14. A gas sensor according to claim 9, wherein a pump cell unit including said first oxygen pump means is formed separately from a sensor cell unit including said oxygen concentration detection element, said second processing space, said combustible gas component concentration detection means, and said second oxygen pump means; and said pump cell unit and said sensor cell unit are joined together via a bonding material.

15. A gas sensor according to claim 14, wherein a pump-cell-side fitting portion is formed in said pump cell unit, and a sensor-cell-side fitting portion to be engaged with the pump-cell-side fitting portion is formed in said sensor cell unit; and said pump cell unit and said sensor cell unit are joined at the pump-cell-side fitting portion and the sensor-cell-side fitting portion.

16. A gas sensor according to claim 1, wherein said oxygen concentration detection element comprises an oxygen-ion-conductive solid electrolyte having electrodes formed on both surfaces thereof including an electrode referred to as a first electrode exposed to said first processing space;

the first electrode is formed of a porous metal of Pt—Au alloy, Pt—Ag alloy, or Pt.

17. A gas sensor system comprising:

a gas sensor comprising:

a first processing space and a first gas passage for introducing a measurement gas into said first processing space;

a second processing space and a second gas passage for introducing a gas contained in said first processing space into said second processing space;

an oxygen concentration detection element for measuring the oxygen concentration of the gas contained in said first processing space;

a first oxygen pump means for pumping out oxygen from said first processing space or pumping oxygen into said first processing space;

a second oxygen pump means for pumping into said second processing space a constant amount of oxygen for measuring the combustible gas component contained in the measurement gas; and a combustible gas component concentration detection means for pumping out oxygen from said second processing space under a constant applied voltage, so that a current output from said combustible gas component concentration detection element varies inversely to the amount of oxygen consumed by combustion of the combustible gas component contained in the gas introduced from said first processing space into said second processing space to thereby provide information regarding a detected concentration of the combustible gas component of the measurement gas;

at least one of said combustible gas component concentration detection means and second oxygen pump means comprises an oxidation catalyst exposed to said second processing space for accelerating combustion of a combustible gas component contained in the gas which has been introduced into said second processing space from said first processing space via the second gas passage;

first oxygen pump element operation control means for controlling said first oxygen pump means so as to adjust the oxygen concentration of the measurement gas in said first processing space detected by said oxygen concentration detection element such that the oxygen concentration falls within a predetermined range;

voltage application means for applying a constant voltage to said combustible gas component concentration detection means; and pumping current supply means for supplying pumping current to said second oxygen pump means.

18. A gas sensor system according to claim 17, further comprising correction means for correcting a detection output from said combustible gas component concentration detection means on the basis of the information regarding the concentration of oxygen in the measurement gas, which is reflected in the pump current of said first oxygen pump means.

19. A gas sensor system according to claim 17, wherein said oxygen concentration detection element is an oxygen concentration cell element formed of an oxygen-ion-conductive solid electrolyte having porous metal electrodes formed on both surfaces thereof including a first electrode serving as a detection-side electrode exposed to said first processing space, and the other electrode serving as an oxygen reference electrode which functions as a self-generation-type oxygen reference electrode, wherein pumping current is caused to flow between the oxygen reference electrode and the detection-side electrode in a direction such that oxygen is pumped toward the oxygen reference electrode, so that the thus-pumped oxygen establishes a predetermined reference oxygen concentration within the oxygen reference electrode;

said combustible gas component concentration detection means comprising an oxygen-ion-conductive solid electrolyte having electrodes formed on both surfaces thereof including a second electrode exposed to said second processing space, the oxygen reference electrode of said oxygen concentration detection element serves as said second electrode; and a current limit circuit is provided in order to prevent an amount of current flowing through said combustible gas component concentration detection means between the second electrode and the oxygen reference electrode from falling outside a predetermined range.

20. A gas sensor system according to claim 19, wherein said current limit circuit prevents an amount of current flowing from the oxygen reference electrode to the second electrode from exceeding a predetermined value.

21. A gas sensor system according to claim 19, wherein said current limit circuit prevents a reverse flow of current from the oxygen reference electrode to the second electrode.

* * * * *